United States Patent [19]

Fukusawa et al.

[11] Patent Number: 4,620,965

[45] Date of Patent: Nov. 4, 1986

[54] HOLLOW FIBER-TYPE ARTIFICIAL LUNG

[75] Inventors: Hiromichi Fukusawa, Funabashi; Takashi Monzen, Tama, both of Japan

[73] Assignee: Terumo Corporation, Tokyo, Japan

[21] Appl. No.: 533,496

[22] Filed: Sep. 16, 1983

[30] Foreign Application Priority Data

Sep. 22, 1982 [JP] Japan .................... 57-163975
Sep. 29, 1982 [JP] Japan .................... 57-168407
Oct. 12, 1982 [JP] Japan .................... 57-177506

[51] Int. Cl.$^4$ .......................................... A61M 1/03
[52] U.S. Cl. ................... 422/46; 210/321.4; 422/48
[58] Field of Search ............... 422/46, 48; 210/436, 210/95, 34.4, 321.3, 472

[56] References Cited

U.S. PATENT DOCUMENTS

| | | | |
|---|---|---|---|
| 3,989,626 | 11/1976 | Bentley et al. | 422/46 |
| 4,138,464 | 2/1979 | Lewin | 422/46 |
| 4,179,380 | 11/1979 | Amicel et al. | 210/321.3 X |
| 4,188,360 | 2/1980 | Kurata | 422/46 |
| 4,242,203 | 12/1980 | Amicel et al. | 210/321.3 X |
| 4,298,358 | 11/1981 | Ruschke | 210/436 X |
| 4,315,819 | 2/1982 | King et al. | 210/321.3 |
| 4,376,095 | 3/1983 | Hagegawa | 422/46 |
| 4,407,563 | 10/1983 | Minott | 350/123 |
| 4,424,190 | 1/1984 | Mather, III et al. | 422/48 X |

FOREIGN PATENT DOCUMENTS

| | | | |
|---|---|---|---|
| 0048943 | 4/1982 | European Pat. Off. | 422/48 |
| 0089122 | 9/1983 | European Pat. Off. | 422/46 |
| 0089748 | 9/1983 | European Pat. Off. | 422/48 |
| 2617208 | 7/1977 | Fed. Rep. of Germany | 422/46 |
| 2374932 | 7/1978 | France | 210/321.3 |
| 50-9299 | 1/1975 | Japan | 422/46 |
| 57-39854 | 3/1982 | Japan | 422/46 |

*Primary Examiner*—Frank Spear
*Attorney, Agent, or Firm*—Frishauf, Holtz, Goodman & Woodward

[57] ABSTRACT

An artificial lung has an axially extending housing which accommodates a bundle of hollow fibers retained within the housing by a pair of walls provided at the ends of the housing. The housing has blood inlet and outlet ports defining a blood chamber within the housing. Oxygen gas is passed through the hollow fibers and blood is passed through the blood chamber so that a gas exchange may take place through the hollow fiber walls. The artificial lung is provided with a blood reservoir chamber integral with the blood chamber and capable of being communicated with the blood chamber, so that blood which has undergone a gas exchange inside the chamber may be stored within the reservoir. A heat exchanger is disposed at a point preceding, following or intermediate the blood chamber and blood reservoir chamber, which construct a blood circuit.

24 Claims, 20 Drawing Figures

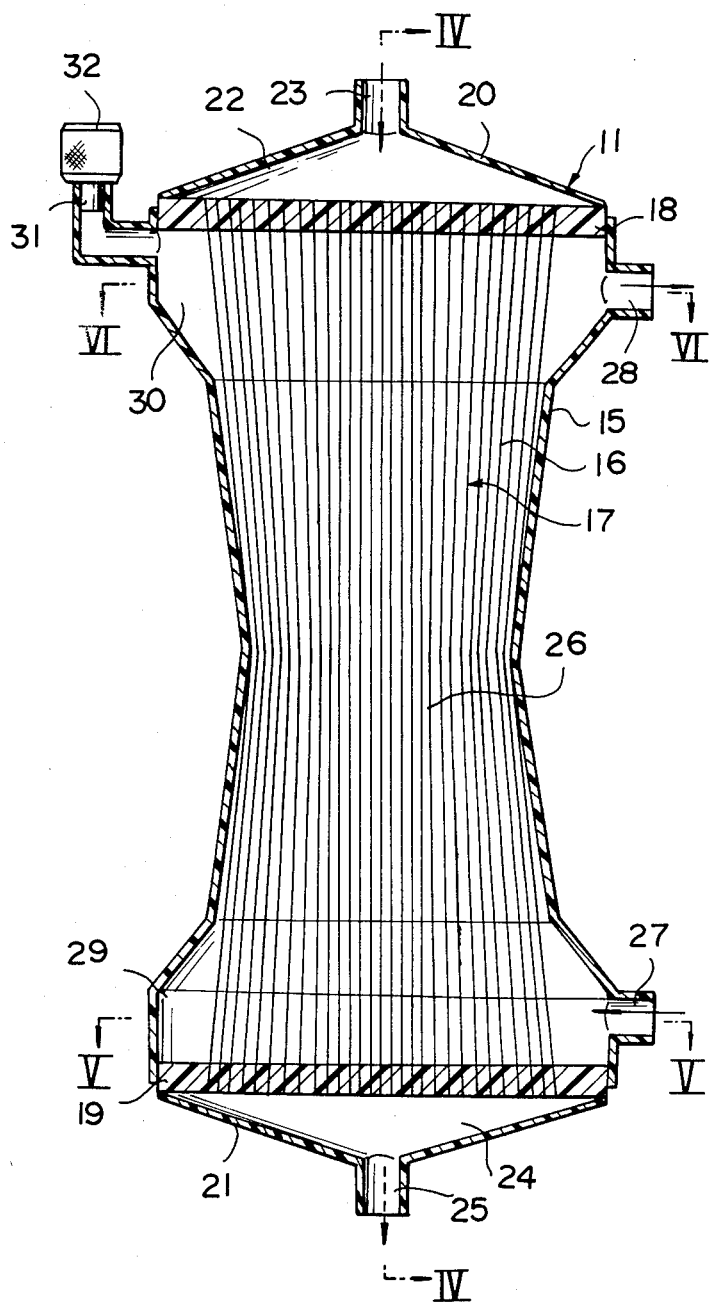

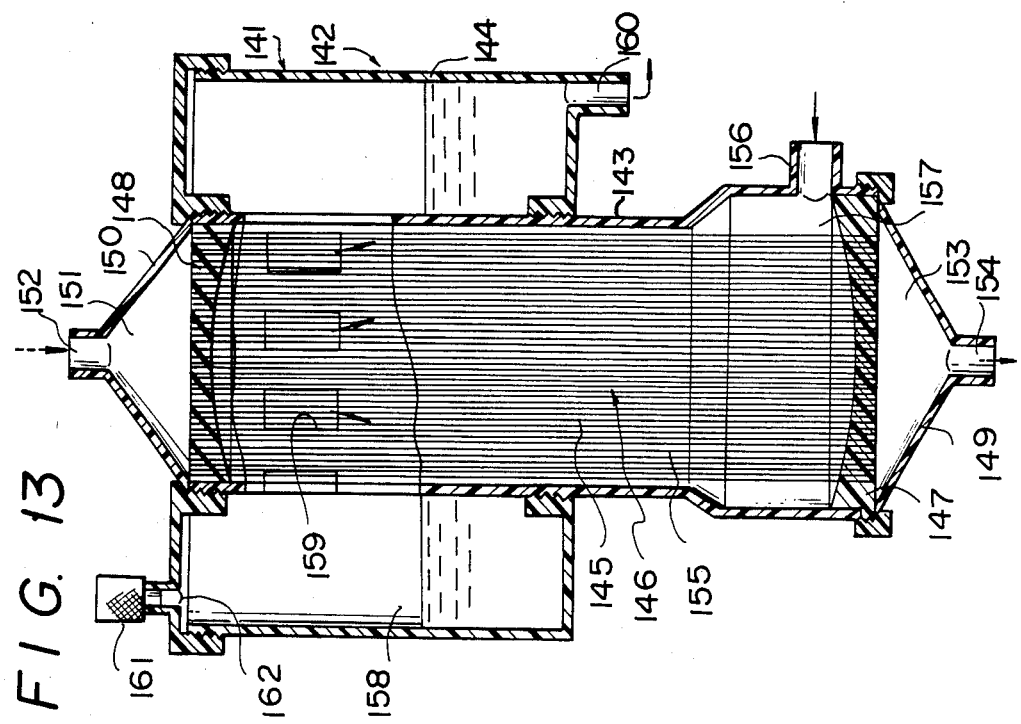
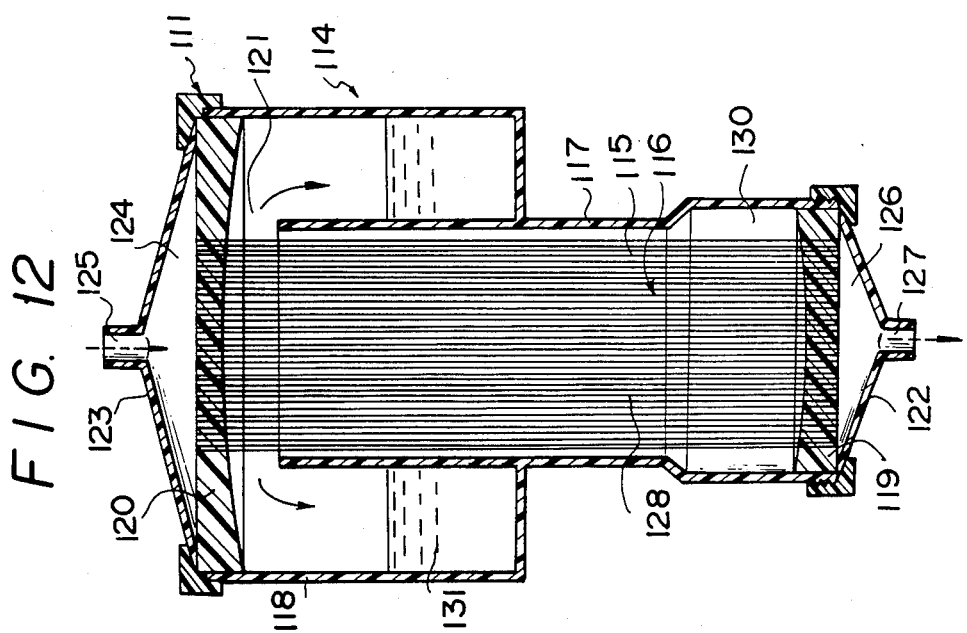

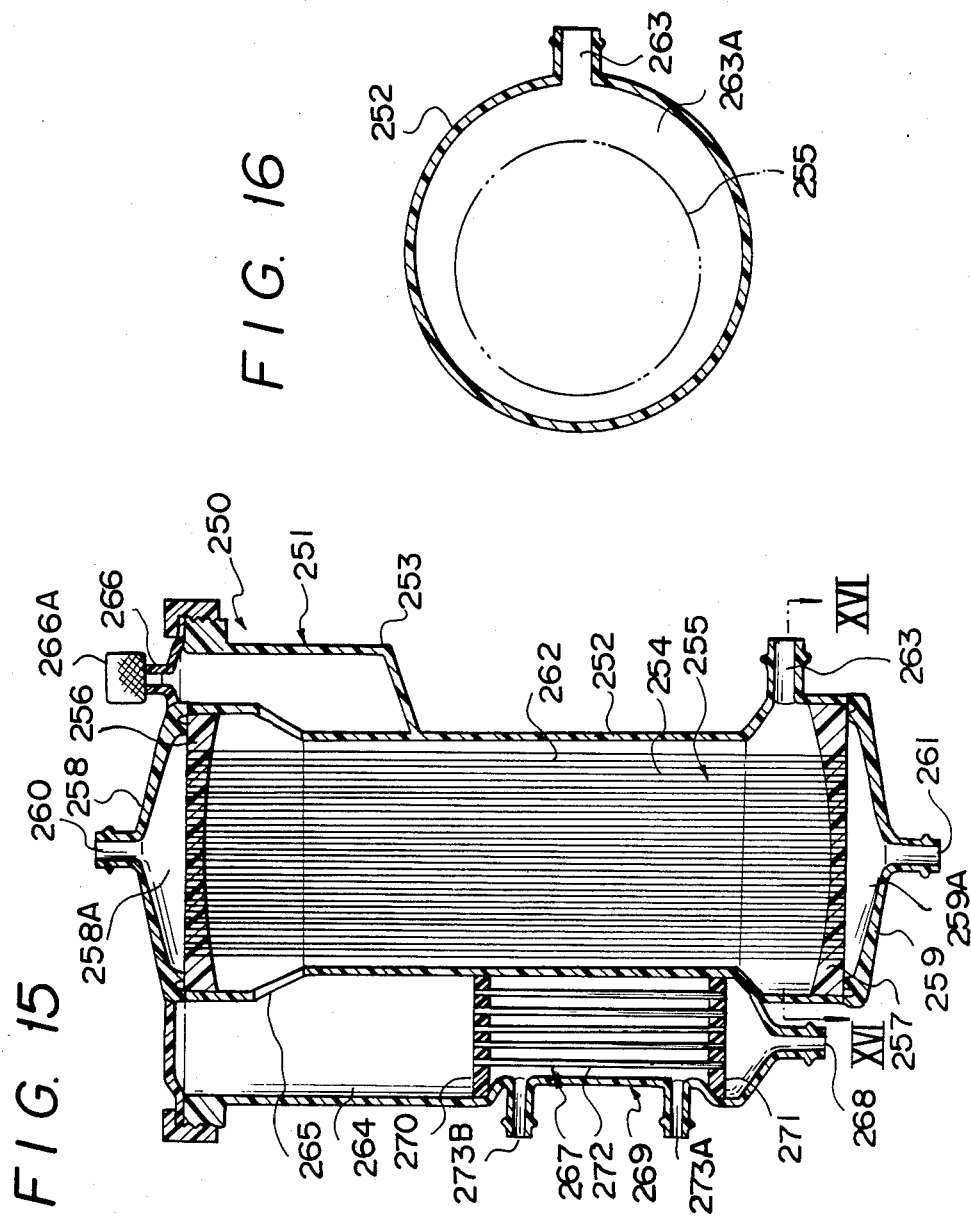

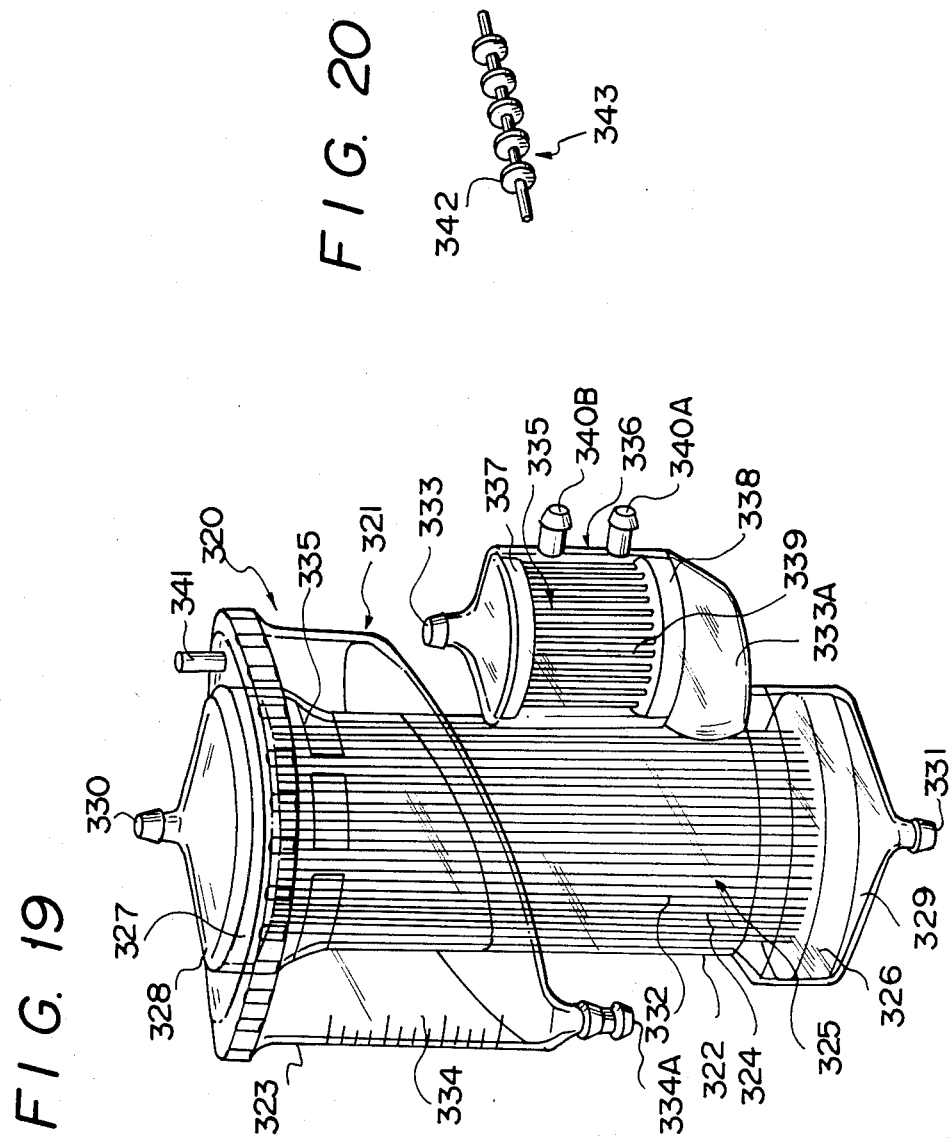

HOLLOW FIBER-TYPE ARTIFICIAL LUNG

BACKGROUND OF THE INVENTION

1. Field of the Invention:

This invention relates to a hollow fiber-type artificial lung used in extracorporeal circulation to remove carbon dioxide from blood and add oxygen to the blood. The invention is applicable to an artificial lung having a blood reservoir chamber and an artificial lung having a heat exchanger.

2. Description of the Prior Art:

Artificial lungs are broadly classified into those of porous type and membrane type. The membrane artificial lung, such as of stacked membrane type, coil type or hollow fiber type, is widely recognized as being superior to the porous-type artificial lung in view of the fact that the blood conveyed through the lung undergoes less hemolysis, albumin degeneration, clotting and affixation, and as being extremely close to the human lung in terms of its operating mechanism. Nevertheless, because the membrane-type artificial lung possesses a number of disadvantages set forth hereinbelow, the artificial lung of porous type is the one used most widely in open-heart surgery at the present time.

In order to obtain sufficient oxygenation with the membrane-type artificial lung currently available, it is required that the blood flow layer be reduced in thickness. This means a narrow blood flow passage and, hence, a large flow passage resistance. In consequence, it is not possible to achieve perfusion of the blood within the artificial lung by utilizing the head developed between the patient and the lung. Accordingly, as shown in FIG. 1, a blood circuit using the membrane-type artificial lung requires that a pump 2 be disposed on the inlet or venous side of the artificial lung, indicated at 1. A blood reservoir 3 and a heat exchanger 4 are also provided. With the blood circuit shown in FIG. 1, however, the magnitude of the pressure adjacent the outlet of the pump 2 is greater than the sum of the pressure loss at the blood feeding catheter and the pressure loss of the artificial lung. The problem that results is an increase in the internal pressure of the circuit on the blood feeding side. A proposed solution to this problem, disclosed in the specification of Japanese Patent Application Laid-Open No. 50-9299, is to pass the blood on the outer side of the hollow fibers. However, the proposed arrangement has not been put into practical use due to difficulties in removing air bubbles developed in the blood in the extracorporeal circuit. Further, there are difficulties in priming and the like in placing the proposed artificial lung into practical use.

The specification of the abovementioned publication discloses a theoretical arrangement for passing oxygen gas on the outer side of hollow fibers, but the arrangement does not maximize the gas exchange capability of the hollow fibers. To obtain a practical system, not only must the gas exchange capability be improved, but the following factors must be taken into consideration. Specifically, through use of the blood reservoir 3 shown in FIG. 1, the extracorporeally circulating blood is temporarily stored so that any air bubbles entrained within the blood may be removed. The reservoir 3 is also necessary for the purpose of maintaining a certain degree of blood flow in the event that the blood extracted from a vein is deficient because of a bend in the associated tubing, or if there is leakage of blood from the system. However, since the blood reservoir 3 is provided in the blood circuit independently of the artificial lung 1 in the conventional membrane-type artificial lung system, the circuit is structurally complex and much time and effort are involved in setting up the circuit and in extracting bubbles during priming. Furthermore, because of the extensive priming and the large amount of blood required to fill the conventional system, it is required that a preliminary transfusion of blood be made into the priming liquid, with which the artificial lung is filled in advance, in order to mitigate dilution of the blood within the patient's body. In particular, the allowable amount of blood available for filling an artificial lung for surgery involving infants and children is small because of low body weight. Therefore, when the membrane-type artificial lung, which requires a large quantity of blood to fill the entire circuit, is used in surgical operations on infants or children, a problem arises in that the total amount of blood available is small.

The heat exchanger 4 in the blood circuit of FIG. 1 is needed for lowering blood temperature during a low body temperature process, and for heating the blood or for keeping the blood warm. However, since the heat exchanger 4, as well as the blood reservoir 3, is provided in the blood circuit independently of the artificial lung 1 in the conventional membrane-type artificial lung system, the circuit becomes even more complex structurally and greater time and effort are required for circuit set up and bubble extraction during priming. Also, as mentioned above, the extensive priming and the large amount of blood required to fill the conventional system require that a preliminary transfusion be made in the priming liquid, with which the artificial lung is filled in advance, to counter dilution of the blood within the patient's body. Because of the small amount of blood available for filling an artificial lung in surgery directed to infants and children, there is a demand for an arrangement capable of greatly diminishing the amount of blood needed to fill the overall blood circuit.

SUMMARY OF THE INVENTION

Accordingly, an object of the present invention is to provide a hollow fiber-type artificial lung which produces a blood flow capable of improving gas exchange efficiency per unit membrane area, which makes possible blood perfusion utilizing the head developed between the patient and the artificial lung, and which effectively removes air evolved during priming and during use.

Another object of the present invention is to provide a hollow fiber-type artificial lung which reduces the amount of blood needed to fill the associated blood circuit, by combining, into a substantially unitary body, a blood chamber and a blood reservoir.

Still another object of the present invention is to provide a hollow fiber-type artificial lung through which is it possible to regulate the amount of extracorporeal circulation.

A further object of the present invention is to provide a hollow fiber-type artificial lung which reduces the amount of blood needed to fill the associated blood circuit, by combining, into a substantially unitary body, a blood chamber and a heat exchanger chamber.

The above and other objects, features and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 3 is a sectional view illustrating an embodiment of a hollow fiber-type artificial lung according to the present invention;

FIG. 12 is a sectional view taken along the line XII—XII of FIG. 11;

FIG. 13 is an enlarged sectional view illustrating another embodiment of the hollow fiber-type artificial lung shown in FIG. 10;

FIG. 15 is a sectional view illustrating a first embodiment of the artificial lung shown in FIG. 14;

FIG. 16 is a sectional view taken along line XVI—XVI of FIG. 14;

FIG. 19 is a perspective view illustrating an artificial lung according to a fourth embodiment; and FIG. 20 is a perspective view illustrating an example of a slender tube having fins forming a heat exchanger.

DESCRIPTION OF THE PREFERRED EMBODIMENTS

Figure 1:
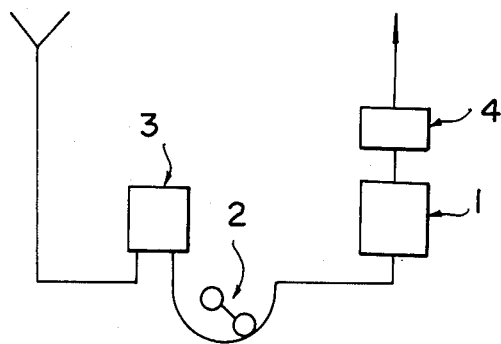
FIG. 1 is a diagram of a blood circuit to which a prior-art membrane-type artificial lung is applied.

According to a first embodiment of the present invention, a hollow fiber-type artificial lung comprises an axially extended housing, a hollow fiber bundle having a multiplicity of hollow fibers accommodated within and along the axial direction of the housing, the hollow fibers forming blood channels between outer wall surfaces of neighboring ones thereof, and being arranged within the housing in such a manner that neighboring blood channels are brought into substantial communication, first and second walls liquid-tightly supporting the hollow fibers at both end portions thereof within the housing, a gas inlet port provided on an outer side of the first or second wall and communicating with the hollow interior of the hollow fibers, the first and second walls, the inner wall of the housing and the outer wall surfaces of the hollow fibers defining a blood chamber, blood inlet and outlet ports communicating with the blood chamber, the blood chamber having a first blood flow passage at a portion adjacent the first wall, the first blood flow passage communicating with the blood inlet port and surrounding the hollow fiber bundle circumferentially at the end portion retained by the first wall, and a second blood flow passage at a portion adjacent the second wall, the second blood flow passage communicating with the blood outlet port and surrounding the hollow fiber bundle circumferentially at the end portion retained by the second wall, a hollow fiber constricting portion for varying the cross sectional area of the blood channels formed between neighboring ones of the hollow fibers, and a gas venting port communicating with the interior of the blood chamber, the venting port being situated higher than the blood outlet port when the artificial lung is in use.

The gas venting port and the blood outlet port are provided at positions substantially symmetrical with respect to the axis of the housing. The second wall has a concave portion on a side facing the second blood flow passage, and the gas venting port is provided in a side wall of the housing adjacent the concave portion of the second wall. The hollow fibers are made of a microporous membrane.

The inner surface of the housing in the vicinity of the blood inlet port is flared outwardly relative to the inner surface of the housing at the intermediate portion thereof, thereby forming the first blood flow passage between the outer periphery of the hollow fiber bundle and the inner surface of the housing, the first blood flow passage being annular in shape. Similarly, the inner surface of the housing in the vicinity of the blood outlet port is flared outwardly relative to the inner surface of the housing at the intermediate portion thereof, thereby forming the second blood flow passage between the outer periphery of the hollow fiber bundle and the inner surface of the housing, the second blood flow passage also being annular in shape.

The flared inner surface of the housing in the vicinity of the blood inlet means is off centered with respect to the hollow fiber bundle so as to increase the distance between the blood inlet means and the hollow fiber bundle, thereby enlarging the flow area of the first blood flow passage facing the blood inlet means. Likewise, the flared inner surface of the housing in the vicinity of the blood outlet means is off centered with respect to the hollow fiber bundle so as to increase the distance between the blood outlet means and the hollow fiber bundle, thereby enlarging the flow area of the second blood flow passage facing the blood outlet means.

The gas venting port includes a detachable filter permeable to gas but impermeable to bacteria.

Figure 2:
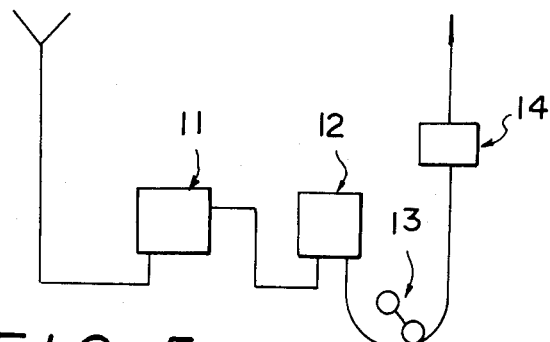
FIG. 2 is a diagram of a blood circuit to which the hollow fiber-type artificial lung of the present invention is applied.
Figure 5:
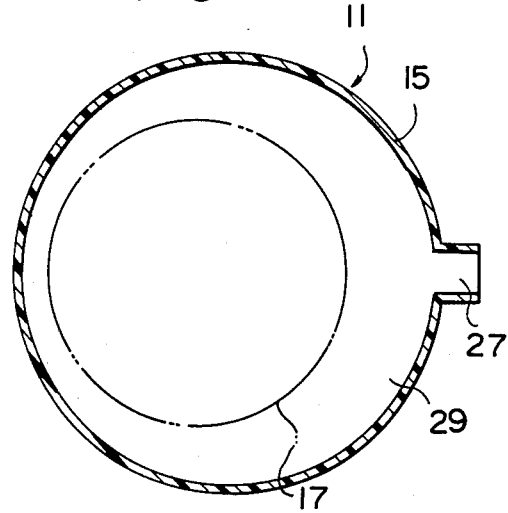
FIG. 5 is a sectional view taken along line V—V of FIG. 3.
Figure 4:
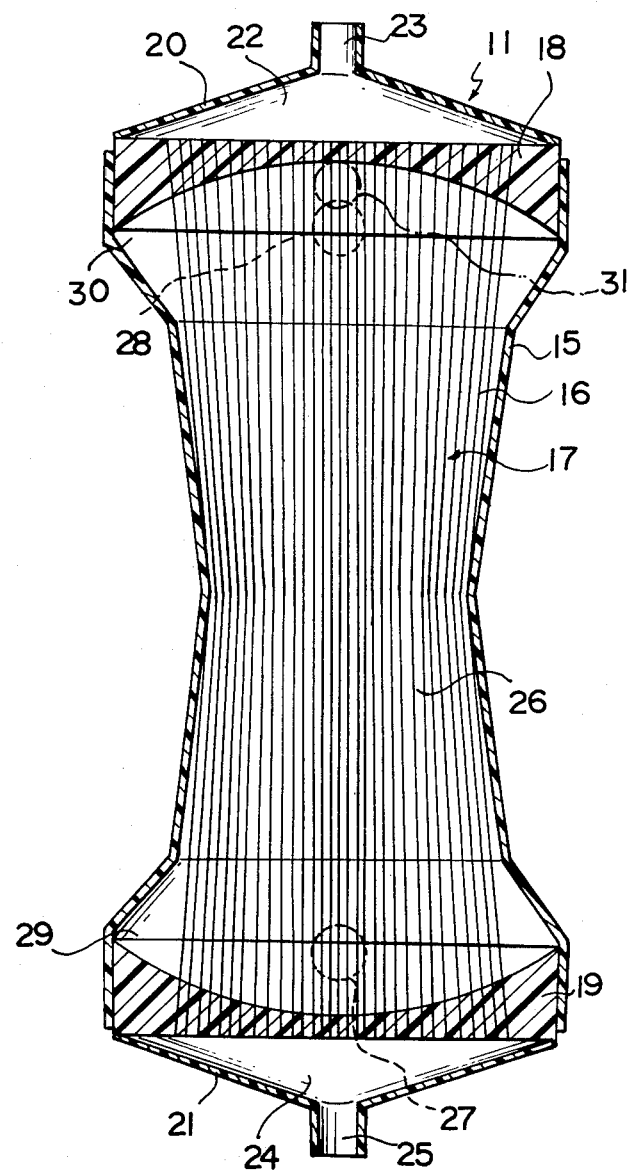
FIG. 4 is a sectional view taken along line IV—IV of FIG. 3.
Figure 6:
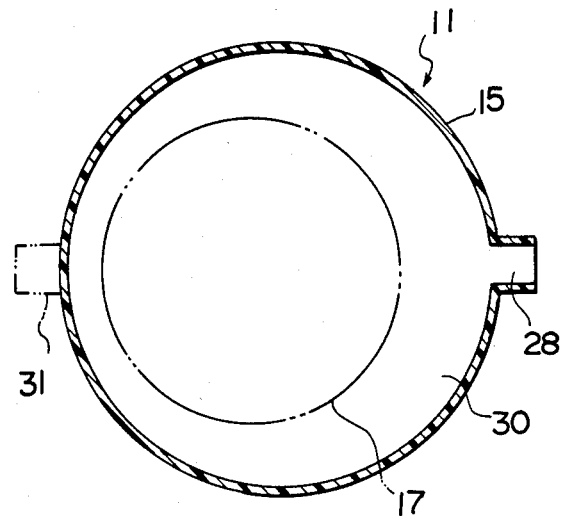
FIG. 6 is a sectional view taken along line VI—VI of FIG. 3.

Reference will now be had to FIGS. 2 through 6 to describe present artificial lung in detail. FIG. 2 is a diagram of a blood circuit to which the hollow fiber-type artificial lung of the present invention is applied, FIG. 3 is a sectional view illustrating an embodiment of a hollow fiber-type artificial lung according to the present invention, FIG. 4 is a sectional view taken along line IV—IV of FIG. 3, FIG. 5 is a sectional view taken along line V—V of FIG. 3, and FIG. 6 is a sectional view taken along line VI—VI of FIG. 3.

As shown in FIG. 2, a blood circuit to which the present invention is applied has an artificial lung 11, a blood reservoir 12, a pump 13 and a heat exchanger 14 through which blood is passed in the order mentioned.

As illustrated in FIGS. 3 through 6, the artificial lung 11 includes a tubular housing 15 accommodating a bundle 17 of hollow fibers 16. The ends of the hollow fibers 16 are retained liquid tightly within the housing 5 via walls 18, 19. A header 20 is attached to one end portion of the housing 15, and a header 21 to the other end thereof. The inner side of the header 20 and the wall 18 define a gas inlet chamber 22 communicating with the space within each of the hollow fibers 16. The inner side of the header 21 and the wall 19 define a gas outlet chamber 24 similarly communicating with the space within each of the hollow fibers. The header 21 is formed to include a gas outlet port 25, and the header 20 is formed to include a gas inlet port 23. Thus, a gas such as oxygen or air supplied from the gas inlet port 23 is capable of being passed through the interior of the hollow fibers 16. It should be noted that the header 21, and hence the gas outlet chamber 24 and gas outlet port 25, is not particularly essential, for an arrangement can be adopted wherein the gas exiting from the hollow fibers 16 is released directly into the atmosphere.

The walls 18, 19, the inner surface of the housing 15, and the outer peripheral surface of the hollow fibers 16 define a blood chamber 26. Formed at the respective ends of the housing 15 in the side thereof are a blood inlet port 27 and a blood outlet port 28, each of which communicates with the blood chamber 26. More specifically, the outer walls of adjacent hollow fibers 16 define channels through which the entrant blood may flow, and neighboring channels communicate with one another owing to the clustered hollow fiber bundle. In consequence, the streams of blood flowing through these channels interfere with one another, causing the blood to flow in a turbulent manner. This makes it possible to achieve a turbulent blood flow at the periphery of the hollow fibers 16 within the blood chamber 26.

The inner surface of the housing 15 at the portion where the blood inlet port 27 is provided is flared outwardly relative to the inner surface of the housing at the intermediate portion thereof, thereby forming an annular blood flow passage 29 between the outer periphery of the hollow fiber bundle 17 and the inner surface of the housing at the flared end, as shown in FIG. 5. This makes it possible for the entrant blood to be distributed to each of the hollow fibers 16 smoothly from the entire outer periphery of the bundle 17 facing the blood flow passage 29. Further, as shown in FIG. 5, the flared inner surface of the housing 15 is off centered with respect to the hollow fiber bundle 17 so as to increase the distance between the blood inlet port 27 and the bundle, thereby enlarging the flow area of that part of the blood flow passage 29 facing the blood inlet port 27. Thus, the flow passage area of the blood flow passage 29 gradually diminishes with an increase in distance from the blood inlet port 27, so that the blood from the blood flow passage 29 is distributed in a uniform amount circumferentially of the hollow fiber bundle 17. This makes it possible for the flow rate of the blood traveling axially of the housing 15 within the blood chamber 26 to be made uniform in relation to the circumferential direction of the hollow fiber bundle 17.

The inner surface of the housing 15 at the portion where the blood outlet port 28 is provided is flared outwardly relative to the inner surface of the housing at the intermediate portion thereof, thereby forming an annular blood flow passage 30 between the outer periphery of the hollow fiber bundle 17 and the inner surface of the housing at this flared end, as shown in FIG. 6. The blood enveloping each of the hollow fibers 16 will therefore flow from the entire outer periphery of the bundle 17, which is facing the blood flow passage 30, into the abovementioned blood channels, and will proceed toward the blood outlet port 28 while mixing of the blood flowing through a plurality of the channels takes place. Further, as shown in FIG. 6, the flared inner surface of the housing 15 at the blood outlet end thereof is off centered with respect to the hollow fiber bundle 17 so as to increase the distance between the blood outlet port 28 and the bundle, thereby enlarging the flow area of that part of the blood flow passage 30 facing the blood outlet port 28. Thus, the flow passage area of the blood flow passage 30 gradually diminishes with an increase in distance from the blood outlet port 28, so that the amount of blood introduced to the blood flow passage 30 is made uniform circumferentially of the hollow fiber bundle 17. This makes it possible for the flow rate of the blood traveling axially of the housing 15 within the blood chamber 26 to be made uniform in relation to the circumferential direction of the hollow fiber bundle 17.

The housing 15 is shaped such that its inner diameter has a minimum value at the mid portion of the housing axially thereof and a gradually larger value as the ends of the housing are approached. Thus, the housing 15 narrows or tapers toward its center from both ends to constrict the outer periphery of the hollow fiber bundle 17 at the central portion thereof in the axial direction. Owing to the constriction of the fiber bundle 17 produced by the tapered shape of the housing 15, a uniform flow of blood through a transverse cross section of the fiber bundle 17 is obtained, and the flow speed varies along the axis of the bundle to promote a turbulent flow condition. This makes it possible to improve gas exchange efficiency. It will be appreciated from FIGS. 3 and 4 that the centrally tapered inner wall of the housing 15 and the inner walls of the housing defining the blood flow passages 29, 30 form a continuous inner wall surface flaring outwardly from the central portion of the housing. This configuration assures that air, which is to be purged from the housing 15 during priming, will travel along the inner wall surface of the housing and exit from a gas venting port 31, described later, without residing in the blood chamber 26. Alternatively, the inner wall of the housing 15 may be flared linearly from, say, the end having the blood inlet port 27 to the end having the blood outlet port 28.

Figure 7:
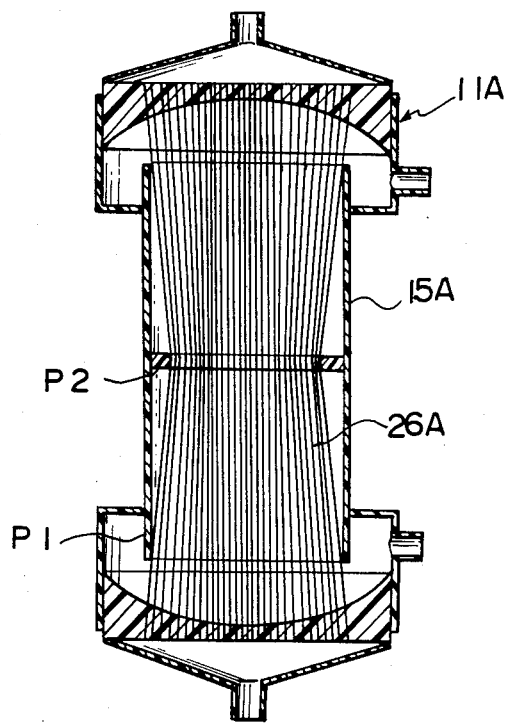
FIG. 7 is a sectional view illustrating a hollow fiber-type artificial lung according to the prior art.

A conventional artificial lung 11A, shown in FIG. 7, has portions P1, P2 projecting discontinuously in the direction of blood flow, these portions being located on the inner surface of a housing 15A defining a blood chamber 26A. With such an arrangement, the air to be vented during priming is entrapped by the projecting portions P1, P2, so that complete discharge of the air from the blood chamber 26A does not take place.

Each of the hollow fibers 16 consists of a microporous membrane. More specifically, each hollow fiber comprises a porous polyolefin resin such as polypropylene or polyethylene, with polypropylene being preferred. In this case, the hollow fibers 16 have a multiplicity of small pores or holes interconnecting the inside and outside of the fiber wall. The hollow fiber has an inner diameter of about 100 to 1,000$\mu$, a wall thickness of about 10 to 500 and preferably 10 to 50$\mu$, and a porosity in the range of amount 20 to 80 percent. With hollow fibers 16 of this kind, membrane resistance to gas flow may be reduced and an excellent gas exchange performance obtained because the gas flow occurs as a volume flow. It should be noted that the hollow fibers 16 need not necessarily consist of a microporous membrane. For example, use can be made of a silicone membrane that permits travel of a gas by dissolution or diffusion.

The packing rate of the housing 15 having hollow fibers of the foregoing type is as specified by the following formula:

$$\text{packing rate (\%)} = \frac{\text{total cross-sectional area of fibers}}{\text{housing cross-sectional area}} \times 100$$

More specifically, $$\text{packing rate } P(\%) = \left(\frac{1r}{2}\right)^2 \pi n / \left(\frac{1a}{2}\right)^2 \pi \times 100$$

where r represents the outer diameter of the hollow fibers, n the number of hollow fibers enclosed within the housing, and a the inner diameter of the housing. The preferred packing rate at the end portions of the housing, namely at the portions of maximum diameter, is 20 to 50%. The preferred packing rate at the centrally constricted portion of the housing is from 1.2 to 4 times the packing rate at the housing end portions. If the packing rate at the housing end portions is less than 20%, there is little surface contact with the outer wall of the hollow fibers and the blood flow is too linear. The result is an unsatisfactory gas exchange performance. If the packing rate at the housing end portions is greater than 50%, on the other hand, the flow of blood is impeded, giving rise to an excessive pressure loss. In a case where the centrally constricted portion is provided, it is necessary to increase the packing density at the constricted portion by at least 1.2 times. A figure below 1.2 times will make it difficult for the blood to flow in the desired turbulent manner, while a packing ratio greater than four times end portion packing ratio, or in excess of 80%, will give rise to an undesirable pressure loss.

The hollow fiber-type artificial lung most preferred has 40,000 hollow fibers, each having an outer diameter of 250 μm, enclosed within a housing the inner diameter of which is 80.0 mm at the end portions and 64.0 mm at the constricted portion thereof. The packing rate is 39.1% at the end portions and 61.0% at the constricted portion.

The walls 18, 19 are formed by a centrifugal injection process in the following manner. First, a multiplicity of the hollow fibers 16, which are longer than the housing 15, are prepared, both open ends of the fibers are plugged with a highly viscous resin, and the fibers are then placed side by side within the housing 15. Thereafter, with both ends of the hollow fibers completely covered, a polymeric potting agent is poured in from both ends of the housing 15 while the housing is being rotated about a center of rotation decided by the longitudinal direction of the housing, under a condition in which the central axis of the housing is situated in the direction of the radius of rotation. After the poured resin has hardened, the outer faces of the resin are cut off by means of a sharp blade to expose both open ends of the hollow fibers 16. This completes the formation of the walls 18, 19. As will be understood from FIGS. 3 and 4, the sides of the walls 18, 19 facing the blood chamber 26 define cylindrical concavities.

The housing 15 is provided with a gas venting port 31 communicating with the blood chamber 26, the port being situated higher than the blood outlet port 28 when the artificial lung is in use. The gas venting port 31 is fitted with a detachable filter 32 permeable to air but not to bacteria. The filter 32 is removed during priming and reattached after priming and serves to prevent bacterial contamination of the artificial lung 11 during the venting of air evolved when the artificial lung is used.

During priming, the gas venting port 31 allows air to escape from the interior of the blood circuit and artificial lung 11, which air is displaced by a filling liquid such as a physiologic saline. Following the removal of air, the port 31 is plugged to form a hermetic seal.

Figure 8:
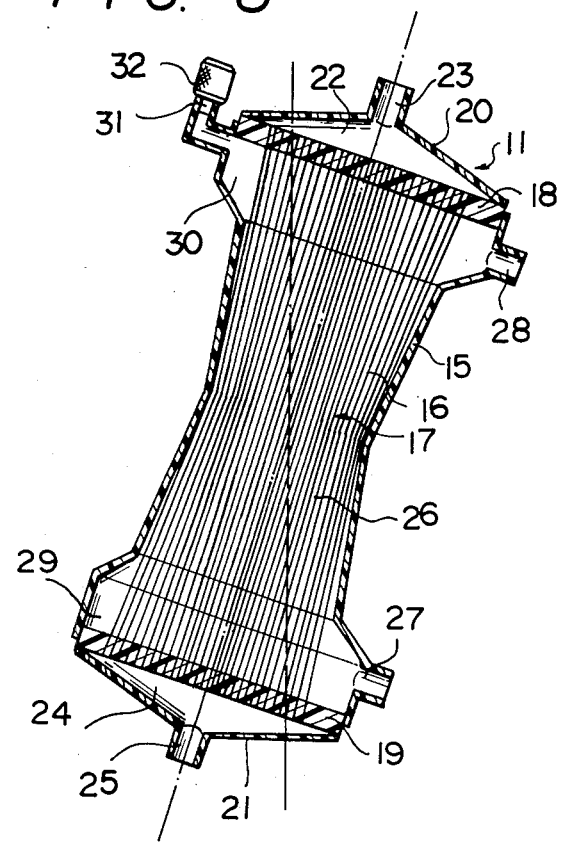
FIG. 8 is a sectional view showing the disposition of the hollow fiber-type artificial lung of the present invention during priming.

The gas venting port 31 and blood outlet port 28 are provided at positions symmetrical with respect to the axis of the housing 15. During priming, as shown in FIG. 8, the central axis of the artificial lung 11 is tilted in a plane which contains both the gas venting port 31 and blood outlet port 28, whereby the gas venting port 31 is placed higher than the blood outlet port 28 to assure and facilitate the discharge of air. The gas venting port 31 is located in the side wall of the housing 15 at a point adjacent the concave surface of the wall 18, as best shown in FIG. 4, so as to communicate with the uppermost part of the blood chamber 26. This makes possible the complete discharge of air during priming, as well as the complete discharge of air which occurs when the artificial lung is used, as when air that remains in the blood circuit connecting joints flows into the artificial lung during use. It should be noted that the gas venting port may be so provided as to penetrate the center of the wall 18.

The operation of the artificial lung shown in FIGS. 3 through 6 will now be described. The artificial lung is for use in, e.g., open-heart surgery, and is installed in a blood circulating circuit of the kind shown in FIG. 2. Ordinarily, blood is extracted at a flow rate of 4 l/ min.

First, prior to introducing blood into the artificial lung 11, physiologic saline mixed with heparin is introduced from the blood inlet port 27 to exclude all air from the blood chamber 26 within the artificial lung 11. During this process, a tube communicating with the blood reservoir will be connected to the gas venting port 31, from which the filter 32 has been removed, and the blood outlet port 28 is either connected to a tube in the same manner as the gas venting port 31, or otherwise sealed by means of a cap or the like. Following the complete purging of the air from the interior of the artificial lung 11, the filter 32 is fitted into the gas venting port 31 which is then sealed by means of a cap, not shown. Blood is introduced from the patient into the artificial lung 11 from the blood inlet port 27 at a predetermined head (on the order of 1 m). The entrant blood impinges upon the outer walls of the hollow fibers 16 near the blood inlet port 27 and flows into the annular blood flow passage 29 defined within the artificial lung. Owing to the force of gravity and the 1 m head, the blood rises within the blood chamber 26. As this proceeds, an exchange is effected between the carbon dioxide contained in the blood and oxygen, which enters from the gas inlet port 23 through the hollow fibers 16. The oxygenated blood flows out of the blood outlet port 28 through the blood flow passage 30, is held in the reservoir 12 (FIG. 2) and then, under the influence of the blood feeding pump 13, is heated or cooled by the heat exchanger 14 before being fed back into the patient.

Any air that appears in the artificial lung 11 during the feeding of the blood, which air is primarily the result of residual air from the tube connections of the blood circuit, flows in from the blood inlet port 27 together with the entering blood, rises within the blood chamber 26 and collects in the concave portion of the wall 18 at the upper end of the blood flow path 30. The collected air is released to the outside through the filter 32 by removing the cap from the gas venting port 31. At such time the artificial lung 11 preferably is tilted, as shown in FIG. 8, to bring the gas venting port 31 to a position higher than that of the blood outlet port 28.

The actions and effects of the artificial lung 11 shown in FIGS. 3 through 6 and in FIG. 8 will now be set forth.

As described hereinabove, the hollow fiber-type artificial lung 11 of the invention comprises an axially extended housing, a hollow fiber bundle having of a multiplicity of hollow fibers accommodated within and along the axial direction of the housing, the hollow fibers forming blood channels between outer wall surfaces of neighboring ones thereof, and being arranged within the housing in such a manner that neighboring blood channels are brought into substantial communication, first and second walls liquid-tightly supporting the hollow fibers at both end portions thereof within the housing, a gas inlet port provided on an outer side of the first or second wall and communicating with the hollow interior of the hollow fibers, the first and second walls, the inner wall of the housing and the outer wall surfaces of the hollow fibers defining a blood chamber, blood inlet and outlet ports communcating with the blood chamber, the blood chamber having a first blood flow passage at a portion adjacent the first wall, the first blood flow passage communciating with the blood inlet port and surrounding the hollow fiber bundle circumferentially at the end portion retained by the first wall, and a second blood flow passage at a portion adjacent the second wall, the second blood flow passage communciating with the blood outlet port and surrounding the hollow fiber bundle circumferentially at the end portion retained by the second wall, a hollow fiber constricting portion for varying the cross sectional area of the blood channels formed between neighboring ones of the hollow fibers, and a gas venting port communicating with the interior of the blood chamber, the venting port being situated higher than the blood outlet port when the artificial lung is in use. Owing to such construction, gas exchange takes place while the blood is flowing in a turbulent state, making it possible to improve the gas exchange performance per unit membrane area. In addition, the blood flow resistance interiorly of the blood chamber does not take on a large magnitude, so that perfusion of the blood may be achieved owing to the head developed between the patient and the artificial lung.

Further, since the gas venting port and the blood outlet port are provided at positions substantially symmetrical with respect to the axis of the housing, air can be discharged from the artificial lung reliably and with ease during priming by placing the gas venting port higher than the blood outlet port, this being accomplished by tilting the central axis of the artificial lung in a plane containing the gas venting port and gas outlet port. The gas venting port is provided in a side wall of the housing adjacent the concave portion of the second wall. Consequently, the gas venting port communicates with the uppermost end of the blood chamber, making it possible to completely discharge air during priming, as well as air which occurs during use. The hollow fibers are made of a microporous membrane to reduce the resistance of the membrane to traveling gases, and to enhance the gas exchange performance.

In the artificial lung, the inner surface of the housing where the blood inlet port is provided is flared outwardly relative to the inner surface of the housing at the intermediate portion thereof, thus forming the annular first blood flow passage between the outer periphery of the hollow fiber bundle and the inner surface of the housing. This makes it possible for the entrant blood to be distributed to each of the hollow fibers smoothly from the entire outer periphery of the bundle facing the first blood flow passage. The inner surface of the housing where the blood outlet port is provided is flared outwardly relative to the inner surface of the housing at the intermediate portion thereof, thus forming the annular second blood flow passage between the outer periphery of the hollow fiber bundle and the inner surface of the housing. This makes it possible for the blood enveloping each of the hollow fibers to be introduced smoothly from the entire outer periphery of the fiber bundle facing the second blood flow passage, into the blood outlet port.

The flared inner surface of the housing in the vicinity of the blood inlet port is off centered with respect to the hollow fiber bundle so as to increase the distance between the blood inlet port and the hollow fiber bundle, thereby enlarging the flow area of the first blood flow passage facing the blood inlet port. As a result, the blood from the blood flow passage is distributed in a uniform amount circumferentially of the hollow fiber bundle, making it possible for the flow rate of the blood traveling axially of the housing within the blood chamber to be made uniform in relation to the circumferential direction of the hollow fiber bundle. Similarly, the flared inner surface of the housing in the vicinity of the blood outlet port is off centered with respect to the hollow fiber bundle so as to increase the distance between the blood outlet port and the hollow fiber bundle, thereby enlarging the flow area of the second blood flow passage facing the blood outlet port. As a result, the amount of blood introduced to the blood flow passage is made uniform circumferentially of the hollow fiber bundle, making it possible for the flow rate of the blood traveling axially of the housing within the blood chamber to be made uniform in relation to the circumferential direction of the hollow fiber bundle.

Further, the gas venting port of the artificial lung includes a detachable filter permeable to gas but impermeable to bacteria. This prevents baterial contamination of the artificial lung when venting air evolved during use of the artificial lung.

Another embodiment of the hollow fiber-type artificial lung shown in FIGS. 3 through 6 will now be described.

In this embodiment, the artificial lung in equipped with a blood reservoir chamber. Specifically, the hollow fiber-type artificial lung comprises an axially extended housing, a hollow fiber bundle having of a multiplicity of hollow fibers accommodated within and along the axial direction of the housing, the hollow fibers forming blood channels between outer wall surfaces of neighboring ones thereof, and being arranged within the housing in such a manner that neighboring blood channels are brought into communication, first and second walls liquid-tightly supporting the hollow fibers at both end portions thereof within the housing, the first and second walls, the inner wall of the housing and the outer wall surfaces of the hollow fibers defining a blood chamber, a blood inlet port provided in a side wall of the housing in the vicinity of the first wall and communicating with the blood chamber, a blood reservoir chamber provided in the vicinity of the second wall and communicating with the blood chamber, a blood outlet port communicating with the blood reservoir chamber, and a gas inlet port provided on an outer side of at least one of the first and second walls and communicating with the hollow interior of the hollow fibers.

The artificial lung includes a gas venting port communicating the blood reservoir chamber with the atmosphere.

The blood reservoir chamber has an outer wall comprising a rigid material, a side surface of the outer wall having graduations. The blood reservoir chamber is so adapted that, when blood is introduced from the blood inlet port so as to rise within the blood chamber, the blood will flow downwardly into the blood reservoir chamber from the blood chamber and will be collected within the blood reservoir chamber.

The inner surface of the housing in the vicinity of the blood inlet port is flared outwardly relative to the inner surface of the housing at the intermediate portion thereof, thus forming an annular blood flow passage between the outer periphery of the hollow fiber bundle and the inner surface of the housing. The flared inner surface of the housing in the vicinity of the blood inlet port is off centered with respect to the hollow fiber bundle so as to increase the distance between the blood inlet port and the hollow fiber bundle, thereby enlarging the flow area of the blood flow passage facing the blood inlet port.

The housing comprises an inner cylinder defining the blood chamber, and an outer cylinder surrounding a portion of the inner cylinder for defining the blood reservoir chamber between itself and the inner cylinder, the first wall being retained in the inner cylinder, the second wall being retained in the outer cylinder. Alternatively, the first and second walls may both be retained in the inner cylinder.

The hollow fibers are made of a microporous membrane. The gas venting port has a filter permeable to gas but impermeable to bacteria.

Figure 9:
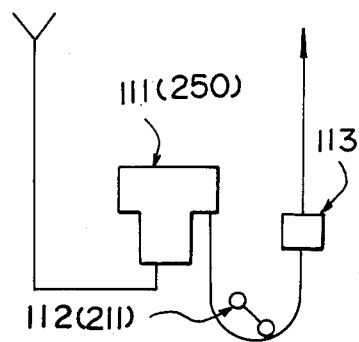
FIG. 9 is a diagram of a blood circuit in a case where the present invention is applied to a hollow fiber-type artificial lung having a blood reservoir chamber.
Figure 11:
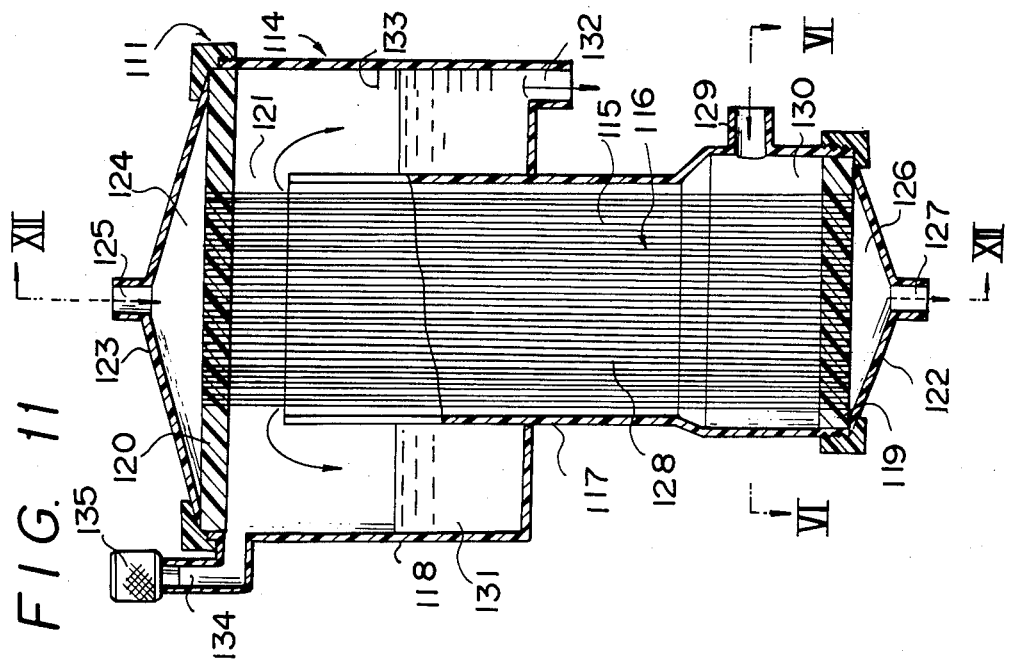
FIG. 11 is a sectional view showing the hollow fiber-type artificial lung of FIG. 10.
Figure 10:
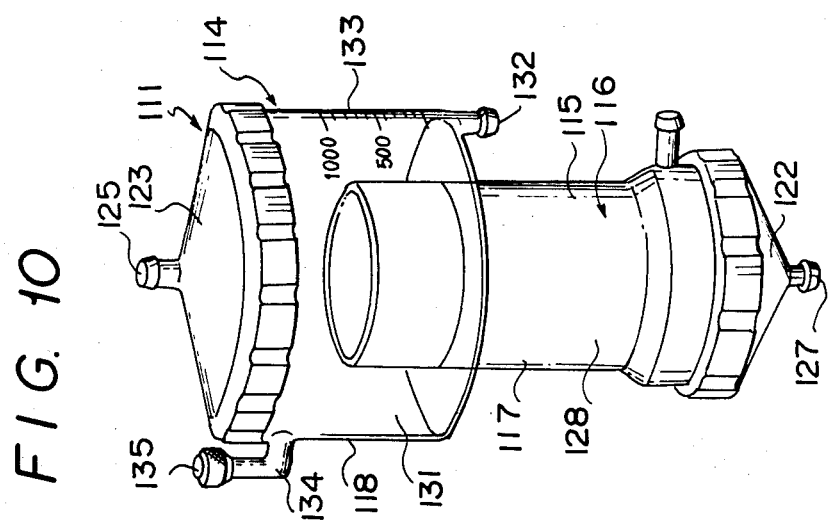
FIG. 10 is a perspective view illustrating an embodiment of a hollow fiber-type artificial lung according to one application of the present invention.

Reference will now be had to FIGS. 9 through 12 to describe the artificial lung in detail. FIG. 9 is a diagram of a blood circuit to which the hollow fiber-type artificial lung is applied, FIG. 10 is a perspective view the embodiment of the hollow fiber-type artificial lung according to one application of the present invention, FIG. 11 is a sectional view showing the hollow fiber-type artificial lung of FIG. 10, and FIG. 12 is a sectional view taken along the line XII—XII of FIG. 11.

As shown in FIG. 9, a blood circuit to which the present invention is applied has an artificial lung 111, a pump 112 and a heat exchanger 113 through which blood is passed in the order mentioned.

As illustrated in FIGS. 10 through 12, the artificial lung 111 includes a housing 114 the hollow interior of which accommodates a bundle 116 of hollow fibers 115. The hollow fibers 115, similar to the hollow fibers 16 described earlier, are made of a microporous membrane, silicone membrane or the like. Reference should be had to the earlier description for further details. Also, as described above with reference to FIGS. 3 through 6, the hollow fibers 115 are accommodated within the housing 114 in such a manner that entrant blood will flow therethrough in a turbulent manner. The housing 114 comprises an internal cylinder 117 which receives the hollow fiber bundle 116 substantially in its entirety, and an outer cylinder 118 receiving the upper portion of the inner cylinder 117 substantially coaxially. The inner and outer cylinders 117, 118 are formed from a rigid material such as acryl-styrene copolymer, polycarbonate or polystyrene. The upper edge portion of the inner cylinder 117 and a wall 120 define an annular, continuous and circumferentially extending communication passage 121. Further, the inner cylinder 117 and the outer cylinder 118 define a blood reservoir chamber 131, which is communicated with a blood chamber 128 via the passage 121. A blood outlet port 132 communicating with the blood reservoir 131 is formed on the outer cylinder 118 at the lowermost position thereof. Here the side of the outer cylinder 118 is provided with engraved graduations 133 for indicating an amount of blood which will collect within the reservoir chamber, as described later.

The volume of the blood reservoir chamber 131 is such that a certain degree of blood flow will be maintained in the event that the blood extracted from a vein is deficient because of a bend in the associated tubing, or if there is leakage of blood from the system. Specifically, the blood reservoir chamber 131 is arranged to have a volume such that the upper level of the collected blood will not rise to a position higher than the upper edge of the inner cylinder 117, even if the amount of blood collected is enough for half of the extracorporeal blood circulation rate (ml/min) planned for safety. When blood flows into the inner cylinder 117 from a blood inlet port 129 and rises within the blood chamber 128, the blood from the blood chamber 128 eventually overflows from the upper edge of the inner cylinder 117 and collects within the blood reservoir chamber 131. By designing it so that the blood reservoir chamber 131 has the above-described volume, the blood which collects within the blood reservoir chamber does not exert any pressure upon the blood rising in the blood chamber 128.

The outer cylinder 118 is provided at its upper portion with a gas vent 134 capable of communicating the blood reservoir chamber 131 with the outside air. The gas vent 134 is fitted with a filter which is permeable to air but impermeable to bacteria, thereby preventing bacterial contamination of the artificial lung 111 during use.

With the artificial lung 111 shown in FIGS. 10 through 12, the hollow interior of each hollow fiber 115 serves as a gas flow passage, while the blood chamber 128 is formed at the outer periphery of the hollow fibers 115. As a result, the entrant blood is subjected to gas exchange in the blood chamber 128 while the blood flows in a turbulent manner, and the membrane area contacting the blood is increased by an amount corresponding to the difference between the inner and outer diameters of the hollow fibers 115. Thus, the oxygenation capability per membrane area is raised so that it is possible to reduce the membrane area required to obtain a given oxygenation capability. Further, since the blood flow paths forming the blood chamber 128 are not narrowed, there is little resistance to the flow of blood within the blood chamber 128. This makes it possible to achieve perfusion of the blood within the artificial lung 111 by virtue of the head developed between the patient and the artificial lung 111, as shown in the blood circuit of FIG. 9. Accordingly, the internal circuit pressure on the blood feeding side is solely the pressure of the blood feeding catheter portion, thereby eliminating the possiblity of accelerated hemolysis and damage to the blood circuit connections. In addition, owing to the unnarrowed blood flow paths in the blood chamber 128, the extraction of bubbles during priming can be carried out quickly and easily.

As mentioned earlier, the hollow fibers 115 consist of a microporous membrane. If water vapor contained within the blood should penetrate into the hollow fibers 115 through the membranous walls thereof, the water vapor will not form dew within the apparatus owing to the temperature, on the order of 37° C., of the blood flowing by the outer periphery of the hollow fibers 115. Thus, there will be no decline in the effective membrane area of the hollow fibers 115 and, hence, no reduction in gas exchange performance.

Since the artificial lung 111 is provided with the internal blood reservoir chamber 131 communicating with the blood chamber 128, the blood circuit takes on the simple arrangement shown in FIG. 9, the circuit can be set up quickly in a simple manner, and the extraction of bubbles during priming can proceed rapidly without obstruction. In addition, the blood circuit in which the artificial lung 111 is used requires little priming and only a small amount of blood for filling, and a preliminary transfusion is unnecessary. In particular, the artificial lung 111 may be used to perform open-heart surgery, without a transfusion, even in the case of infants or children for which the allowable blood filling quantity is low.

FIG. 13 is a sectional view illustrating a hollow fibertype artificial lung 141 according to another embodiment of the present invention. The artificial lung 141 includes a housing 142 comprising an inner cylinder 143 and an outer cylinder 144. The inner cylinder 143 accommodates a bundle 146 of a multiplicity of hollow fibers 145. The ends of the hollow fibers 145 are retained liquid tightly within the inner cylinder 143 via walls 147, 148 retained in the upper and lower ends of the inner cylinder 143, respectively. A header 149 is attached to one end portion of the inner cylinder 143, and a header 150 to the other end portion thereof. The inner side of the header 150 and the wall 148 define a gas inlet chamber 151 communicating with the space within each of the hollow fibers 145. The inner side of the header 149 and the wall 147 define a gas outlet chamber 153 similarly communicating with the space within each of the hollow fibers. The header 149 is formed to include a gas outlet port 154, and the header 150 is formed to include a gas inlet port 152. Thus, a gas such as oxygen or air supplied from the gas inlet port 152 is capable of being passed through the interior of the hollow fibers 145.

The walls 147, 148, the inner surface of the inner cylinder 143, and the outer surface of the hollow fibers 145 define a blood chamber 155. The lower end of the inner cylinder 143 is formed to include a blood inlet port 156 in the side thereof, as well as a blood flow passage 157 similar to the blood flow passage 29 in the artificial lung 11 of FIGS. 3 and 4. Thus, blood supplied from the blood inlet port 156 is passed over the periphery of the hollow fibers 145 in the blood chamber 155 in a turbulent state so that a gas exchange may take place.

In the artificial lung 141 of FIG. 13, the outer cylinder 144 is fitted on the inner cylinder 143 from the upper part thereof and encircles the upper end portion of the inner cylinder 143 and the header 150. A blood reservoir chamber 158 is formed between the inner cylinder 143 and the outer cylinder 144. The side wall of that portion of the inner cylinder 143 inside the outer cylinder 144 is provided with a plurality of circumferentially spaced windows or communication passages 159 for communicating the interior of the blood chamber 155 with the interior of the blood reservoir chamber 158. A blood outlet port 160 communicating with the blood reservoir chamber 158 is formed on the outer cylinder 144 at the lowermost position thereof. The outer cylinder 144 is provided at its upper portion with a gas vent 162, having a filter 161, for communicating the blood reservoir chamber 158 with the outside air.

The volume of the blood reservoir chamber 158 is such that the upper level of blood, which collects within the chamber, will remain below the communication passages 159 at all times. As with the artificial lung 111 of FIGS. 10 through 12, the arrangement is such that blood overflows into the blood reservoir chamber 158 from the blood chamber 155. In this case, however, the blood flows out of the communcation passages 159.

Thus, as with the artificial lung 111, the artificial lung 141 of the present embodiment improves the gas exchange performance per unit membrane area of the hollow fibers 145, makes it possible to achieve perfusion of the blood by virtue of the head developed between the patient and the artificial lung 141, and reduces the quantity of blood needed to fill the blood circuit in which the artificial lung is used. In addition, since the inner cylinder 143 retains the pair of walls 147, 148 and accommodates the bundle 146 of hollow fibers 145, and since the outer cylinder 144 is fitted on the inner cylinder 143 from the top part thereof, the overall artificial lung is simplified in construction and easy to manufacture.

The operation of the artificial lung 111 illustrated in FIGS. 10 through 12 will now be described.

First, prior to introducing blood into the artificial lung 111, physiologic saline mixed with heparin is introduced from the blood inlet port 129 to exclude air from the blood chamber 128 within the artificial lung. In this process, a tube communicating with a heat exchanger is connected to the blood outlet port 132 and the gas venting port 134 is sealed. Or, conversely, the tube is connected to the gas venting port 134 (from which the detachable filter 135 is removed), and the blood outlet port 132 is sealed. Alternatively, the tube is bifurcated and connected to both ports 132, 134. Following the complete purging of the air from the interior of the blood chamber, the filter, if it has been removed, is fitted into the gas venting port. Blood taken from the patient at a predetermined head (on the order of 1 m) is mixed with heparin and then introduced into the artificial lung 111 from the blood inlet port 129. Ordinarily, the blood is introduced at a rate of 4 l/min. The entrant blood impinges upon the outer walls of the hollow fibers 116 near the blood inlet port 129 and flows into the blood flow passage 130 defined within the artificial lung. Owing to the force of gravity and the 1 m head, the blood rises within the blood chamber 128. As this proceeds, an exchange is effected between the carbon dioxide contained in the blood and oxygen, which enters from the gas inlet port 125 through the hollow fibers 116. The oxygenated blood overflows from the upper edge of the inner cylinder 117 and is collected in the blood reservoir chamber 131. The gas venting port 134 is open to the air through the filter 135. The amount of blood which exits from the artificial lung is regulated by a change in the amount of blood collected within the blood reservoir chamber. The blood that flows from the blood outlet port 132 is returned to the patient by the blood feeding pump 112 (FIG. 9) following heating or cooling to a suitable temperature by means of the heat exchanger 113.

Any air that appears in the artificial lung 111 during the feeding of the blood, which air is primarily the result of residual air from the tube connections of the blood circuit, flows in from the blood inlet port 129 together with the entering blood, rises within the blood chamber 128, passes through the blood reservoir chamber 131 and is released to the outside through the filter 135 in the gas venting port 134.

The actions and effects of the foregoing artificial lung will now be set forth.

As described, the hollow fiber-type artificial lung, having the blood reservoir chamber, comprises a housing, a hollow fiber bundle having of a multiplicity of hollow fibers for gas exchange accommodated within the housing, first and second walls liquid-tightly supporting the hollow fibers at both end portions thereof within the housing, the first and second walls, the inner wall of the housing and the outer wall surfaces of the hollow fibers defining a blood chamber, a blood inlet port provided in a side wall of the housing in the vicinity of the first wall and communicating with the blood chamber, a blood reservoir chamber provided in the vicinity of the second wall and communicating with the blood chamber, a blood outlet port communcating with the blood reservoir chamber, and a gas inlet port provided on an outer side of at least one of the first and second walls and communicating with the hollow interior of the hollow fibers. Owing to such construction, gas exchange takes place while the blood is flowing in a turbulent state, making it possible to improve the gas exchange performance per unit membrane area. In addition, the blood flow resistance interiorly of the blood chamber is reduced to a small value, so that perfusion of the blood may be achieved owing to the head developed between the patient and the artificial lung. Furthermore, the amount of blood needed to fill the blood circuit is small because the blood chamber and blood reservoir chamber are substantially united.

Since the artificial lung is provided with the blood reservoir chamber, it is possible to regulate the amount of blood during extracorporeal circulation. Since the outer wall of the blood reservoir chamber consists of a rigid material and is provided with graduations indicating the volume of collected blood, one may readily grasp the amount of blood being extracorporeally circulated. Further, the blood reservoir chamber is so adapted that, when blood is introduced from the blood inlet port so as to rise within the blood chamber, the blood will flow downwardly into the blood reservoir chamber from the blood chamber and will be collected within the blood reservoir chamber. Therefore, the collected blood will not exert significant pressure upon the blood moving within the blood chamber.

In the artificial lung, the inner surface of the housing where the blood inlet port is provided is flared outwardly relative to the inner surface of the housing at the intermediate portion thereof, thereby forming an annular blood flow passage between the outer periphery of the hollow fiber bundle and the inner surface of the housing. This makes it possible for the entrant blood to be distributed to each of the hollow fibers smoothly from the entire outer periphery of the bundle facing the blood flow passage.

The flared inner surface of the housing in the vicinity of the blood inlet port is off centered with respect to the hollow fiber bundle so as to increase the distance between the blood inlet port and the hollow fiber bundle, thereby enlarging the flow area of the blood flow passage facing the blood inlet port. As a result, the blood from the blood flow passage is distributed in a uniform amount circumferentially of the hollow fiber bundle, making it possible for the flow rate of the blood traveling axially of the housing within the blood chamber to be made uniform in relation to the circumferential direction of the hollow fiber bundle.

The housing of the artificial lung comprises an inner cylinder defining the blood chamber, and an outer cylinder surrounding a portion of the inner cylinder for defining the blood reservoir chamber between itself and the inner cylinder, the first wall being retained in the inner cylinder, the second wall being retained in the outer cylinder. The result is a comparatively simple construction. Alternatively, the first and second walls may both be retained in the inner cylinder. This affords an even simpler construction and facilitates the manufacture of the artificial lung.

The hollow fibers are made of a microporous membrane to reduce the resistance of the membrane to traveling gases, and to enhance the gas exchange performance. Further, the gas venting port has a filter permeable to gas but impermeable to bacteria. This prevents bacterial contamination of the artificial lung during use.

In another embodiment of the present invention, the hollow fiber-type artificial lung is equipped with a heat exchanger mechanism. Specifically, the artificial lung comprises an axially extended housing, a hollow fiber bundle having a multiplicity of hollow fibers accommodated within and along the axial direction of the housing, the hollow fibers forming blood channels between outer wall surfaces of neighboring ones thereof, and being arranged within the housing in such a manner that neighboring blood channels are brought into substantial communication, first and second walls liquid-tightly supporting the hollow fibers at both end portions thereof within the housing, the first and second walls, the inner wall of the housing and the outer wall surfaces of the hollow fibers defining a blood chamber, a blood inlet means provided in a side wall of the housing in the vicinity of the first wall and having an opening communicating with the blood chamber, a heat exchanger provided integral with a blood flow passage, which is formed by the blood chamber, at least at an upstream, down stream or intermediate portion of said blood flow passage, and gas inlet means provided on an outer side of at least one of the first and second walls.

The housing has a blood outlet port, the blood reservoir being provided on the blood outlet means side. The housing has the heat exchanger which is provided in the blood chamber on the blood outlet means side. The heat exchanger is provided within the blood reservoir.

The heat exchanger comprises a bundle of a multiplicity of slender tubes supported at both ends by a pair of walls. The ends of the tubes are open, so that the hollow interiors of the tubes define blood flow passages. The heat exchanger is so adapted that a heat transfer medium may be passed along the periphery of the tubes.

Alternatively, the heat exchanger comprises a tubular body through the hollow interior of which a heat transfer medium may be passed.

The blood reservoir has a gas vent communicating with the atmosphere, and an outer wall comprising a rigid material.

The hollow fibers are made of microporous membrane.

The housing comprises an inner cylinder accommodating the hollow fibers, and an outer cylinder surrounding a portion of the inner cylinder for defining the blood reservoir between itself and the inner cylinder. The first wall supporting the hollow fibers is retained in the inner cylinder, and the second wall supporting the hollow fibers is retained in the outer cylinder. Alternatively, both walls supporting the hollow fibers are retained in the inner cylinder.

The inner surface of the housing at a portion communicating with the blood inlet means is flared outwardly relative to the intermediate portion of the housing, thereby forming an annular blood flow passage between the outer periphery of the hollow fiber bundle and the inner surface of the housing. The flared inner surface of the housing in the vicinity of the blood inlet means is off centered with respect to the hollow fiber bundle so as to increase the distance between the blood inlet port and the hollow fiber bundle, thereby enlarging the flow area of the blood flow passage facing the blood inlet means.

The artificial lung will now be described with reference to FIGS. 14 through 16.

As shown in FIG. 9, the artificial lung, designated at 250, is installed in a blood circuit together with a pump 211. Blood introduced from the patient's vein passes through these components in the order mentioned.

Figure 14:
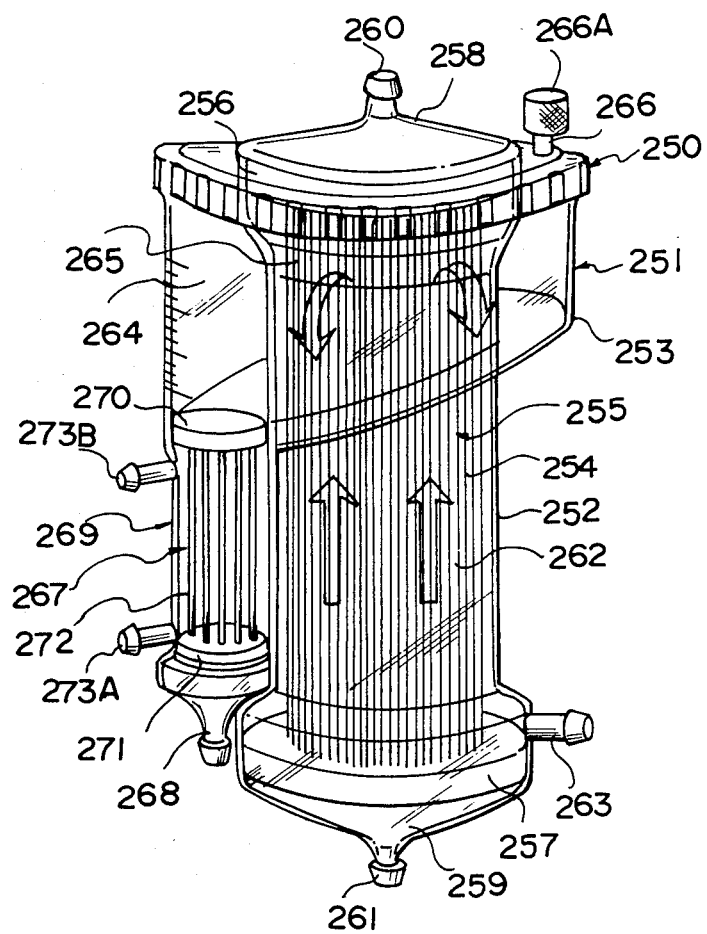
FIG. 14 is a perspective view illustrating an artificial lung, having a heat exchanger, according to an application of the present invention.

As illustrated in FIGS. 14 through 16, the artificial lung 250 includes a housing 251 comprising an inner cylinder 252 and an outer cylinder 253 consisting of a rigid material such as acryl-styrene copolymer, polycarbonate or polystyrene. A bundle 255 of a multiplicity of hollow fibers 254 are accommodated within the inner cylinder 252. The ends of the hollow fibers 254 are retained liquid tightly within the inner cylinder 252 via walls 256, 257 retained in the upper and lower ends of the inner cylinder 252, respectively. A header 258 is attached to one end portion of the inner cylinder 252, and a header 259 to the other end portion thereof. The inner side of the header 258 and the wall 256 define a gas inlet chamber 258A communicating with the space within each of the hollow fibers 254. The inner side of the header 259 and the wall 257 define a gas outlet chamber 259A similarly communicating with the space within each of the hollow fibers. The header 259 is formed to include a gas outlet port 261, and the header 258 is formed to include a gas inlet port 260. Thus, a gas such as oxygen or air supplied from the gas inlet port 260 is capable of being passed through the interior of the hollow fibers 254. It should be noted that the header 259, and hence the gas outlet chamber 259A and gas outlet port 261, is not particularly essential, for an arrangement can be adopted wherein the gas exiting from the hollow fibers 254 is released directly into the atmosphere.

The housing 251, the outer surface of the hollow fibers 254, and the walls 256, 257 define a blood chamber 262. The inner cylinder 252 is formed to include a blood inlet port 263 in the vicinity of the wall 257, the port communicating with the blood chamber 262. As described above with reference to FIGS. 3 through 6, the hollow fibers 254 are accommodated within the housing 251 in such a manner that entrant blood will flow therethrough in a turbulent manner.

The inner surface of the inner cylinder 252, which forms the housing 251, is flared outwardly in the vicinity of the blood inlet port 263 relative to the inner surface of the inner cylinder 252 at the, intermediate portion thereof, thus forming an annular blood flow passage 263A between the hollow fiber bundle 255 and the inner surface of the inner tube, as shown in FIG. 16. This makes it possible for the entrant blood to be distributed to each of the hollow fibers 254 smoothly from the entire outer periphery of the hollow fiber bundle 255 facing the blood flow passage 263A. The flared inner surface of the inner cylinder 252 in the vicinity of the blood inlet port 263 is off centered with respect to the hollow fiber bundle 255 so as to increase the distance between the blood inlet port 263 and the hollow fiber bundle, thereby enlarging the flow area of the blood flow passage 263A facing the blood inlet port 263. Thus, the flow passage area of the blood flow passage 263A gradually diminishes with an increase in distance from the blood inlet port 263, so that the blood from the blood flow passage 263A is distributed in a uniform amount circumferentially of the hollow fiber bundle 255. This makes it possible for the flow rate of the blood rising in the blood chamber 262 to be made uniform in relation to the circumferential direction of the hollow fiber bundle 255.

With regard to the housing 251, the outer cylinder 253 surrounds the upper end portion of the inner cylinder 252, so that a blood reservoir tank 264 communicating with the blood chamber 262 is defined between the inner and outer cylinders. The side wall of that portion of the inner cylinder 252 inside the outer cylinder 253 is provided with a plurality of circumferentially spaced windows or communication passages 265 for communicating the interior of the inner cylinder 252 with the interior of the reservoir chamber 264. The upper portion of the outer cylinder 253 is formed to include a gas vent 266 having a filter 266A permeable to air but impermeable to bacteria. This prevents bacterial contamination of the artificial lung 250 during use and maintains the interior of the reservoir 264 at atmospheric pressure at all times. The side surface of the reservoir tank 264 is provided with engraved graduations to indicate the amount of blood collected within the reservoir.

The volume of the reservoir tank 264 is such that a certain degree of blood flow will be maintained in the event that the blood extracted from a vein is deficient because of a bend in the associated tubing, or if there is leakage of blood from the system. Specifically, the reservoir tank 264 is constructed to have a volume such that the upper level of the collected blood will not rise to a position higher than the lower edge of the communication passages 265, even if the amount of blood collected is enough for half of the extracorporeal blood circulation rate (ml/min) planned for safety. When blood flows into the inner cylinder 252 from the blood inlet port 263 and rises within the blood chamber 262, the blood eventually overflows from the lower edge of the communication passages 265 and collects within the blood reservoir tank 264. By arranging it so that the blood reservoir 264 has the above-described volume, the blood which collects within the blood reservoir does not exert any pressure upon the blood rising in the blood chamber 262.

A blood outlet port 268 communicates with the interior of the blood reservoir tank 264 through a heat exchanger tank 267, the latter accommodating a heat exchanger 269. The heat exchanger 269 is supported at both ends by respective walls 270, 271 located within the heat exchanger tank 267, and has a bundle of slender tubes 272 whose upper ends open into the reservoir 264 and whose lower ends open into the blood outlet port 268. The hollow interior of each slender tube 272 serves as a blood flow passage, while the outer walls of the slender tubes 272 and the inner sides of the walls 270, 271 define a flow passage for a heat transfer medium. Connecting with the heat transfer medium flow passage are inlet and outlet ports 273A, 273B, respectively, for heating and cooling water. The slender tubes 272 comprise stainless steel or aluminum tubes having a high heat transfer coefficient. The heat exchanger tank 267 of the artificial lung 250 makes it possible to raise or lower blood temperature, or to keep the blood warm.

The hollow fibers 254 are made of a microporous membrane, as described earlier with regard to the hollow fibers 16. It should be noted that the hollow fibers 254 need not necessarily consist of a microporous membrane. For example, use can be made of a silicone membrane that permits travel of a gas by dissolution or diffusion.

The walls 256, 257 are formed by a centrifugal injection process in the same manner as the walls 18, 19 described earlier. The process need not be discussed again here.

Since the artificial lung 250 of FIGS. 14 through 16 incorporates the blood chamber 262, the blood reservoir 264 and heat exchanger tank 267, the blood circuit takes on the simple arrangement shown in FIG. 9, which is similar to the arrangement in which a porous-type artificial lung is used. In addition, the circuit can be set up quickly in a simple manner, and the extraction of bubbles during priming can proceed rapidly without obstruction. Furthermore, the blood circuit in which the artificial lung 250 is used requires little priming and only a small amount of blood for filling. There is also little need to carry out a preliminary transfusion into the priming liquid, such as physiologic saline, with which the artificial lung 250 is filled. In particular, the artificial lung 250 is effective even for infants or children for which the allowable blood filling quantity is low.

In the artificial lung shown in FIGS. 14 through 16, both of the walls 256, 257 supporting the upper and lower ends of the hollow fibers 254 are retained within the inner cylinder 252. However, an arrangement is possible wherein the wall supporting the upper ends of the hollow fibers is retained in the outer cylinder.

Figure 17:
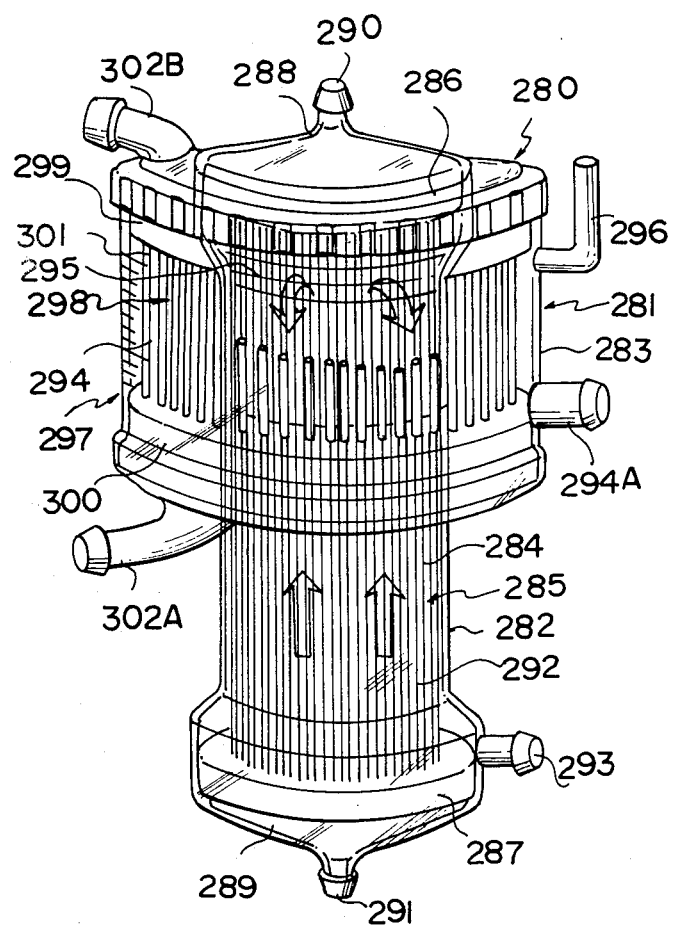
FIG. 17 is a perspective view illustrating an artificial lung according to a second embodiment of the artificial lung shown in FIG. 14.

FIG. 17 is a perspective view illustrating an artificial lung 280, which is an another example of the artificial lung 251 shown in FIGS. 14 through 16.

The artificial lung 280 has a housing 281 comprising an inner cylinder 282 and an outer cylinder 283. A bundle 285 of a multiplicity of hollow fibers 284 are accommodated within the inner cylinder 282. The ends of the hollow fibers 284 are retained liquid tightly within the inner cylinder 282 via walls 286, 287 retained in the upper and lower ends of the inner cylinder 282, respectively. A header 288 is attached to one end portion of the inner cylinder 282, and a header 289 to the other end portion thereof. The inner side of the header 288 and the wall 286 define a gas inlet chamber similar to that formed in the artificial lung 250. The inner side of the header 289 and the wall 287 define a gas outlet chamber similar to that formed in the artificial lung 250. The header 289 is formed to include a gas outlet port 291, and the header 288 is formed to include a gas inlet port 290. The inner wall of the housing 281, the outer wall of the hollow fibers 284, and the walls 286, 287 define a blood chamber 292. The lower end of the inner cylinder 282 is formed to include a blood inlet port 293. Thus, a gas such as oxygen or air supplied from the gas inlet port 290 can be passed through the interior of the hollow fibers 284, while blood supplied from the blood inlet port 293 is passed in a turbulent state along the periphery of the hollow fibers 284 within the blood chamber 292, allowing a gas exchange to take place.

Further, in the artificial lung 280, a blood reservoir 294 is formed, as a portion of the blood chamber 292, between the inner cylinder 282 and outer cylinder 283. The side wall of that portion of the inner cylinder 282 inside the outer cylinder 283 is provided with a plurality of circumferentially spaced windows or communication passages 295 for communicating the blood chamber 292 inside the inner cylinder 282 with the interior of the blood reservoir 294. The outer cylinder 283 is provided at its upper portion with a gas vent 296 communicating with the reservoir 294. The lower portion of the outer cylinder 283 is formed to include a blood outlet port 294A communicating with the reservoir 294. Thus, the blood reservoir 294 is adapted to collect blood which has undergone a gas exchange, similar to the blood reservoir 264 of the artificial lung 250.

The blood reservoir 294 of the artificial lung 280 accommodates a heat exchanger 298 so that it may also function as a heat exchanger tank 297. The heat exchanger 298 comprises a bundle of slender tubes 301 supported at both ends by respective walls 299, 300 located within the heat exchanger tank 297. The ends of the slender tubes 301 open externally of the blood reservoir 294 on the outer sides of the walls 299, 300, the hollow interior of each tube serving as a flow passage for a heat transfer medium. Inlet and outlet ports 302A, 302B for cooling and heating water are connected to the flow passages for the heat transfer medium. Thus, the heat exchanger tank 297 serves to heat, cool or maintain the temperature of blood following the gas exchange.

Thus, as with the artificial lung 250, the artificial lung 280 improves the gas exchange performance per unit membrane area of the hollow fibers 284, makes it possible to achieve perfusion of the blood by virtue of the head developed between the patient and the artificial lung 280, and reduces the quantity of blood needed to fill the blood circuit in which the artificial lung is used. This is because of the blood reservoir 294 and heat exchanger tank 297, which communicates with the blood chamber 292.

Figure 18:
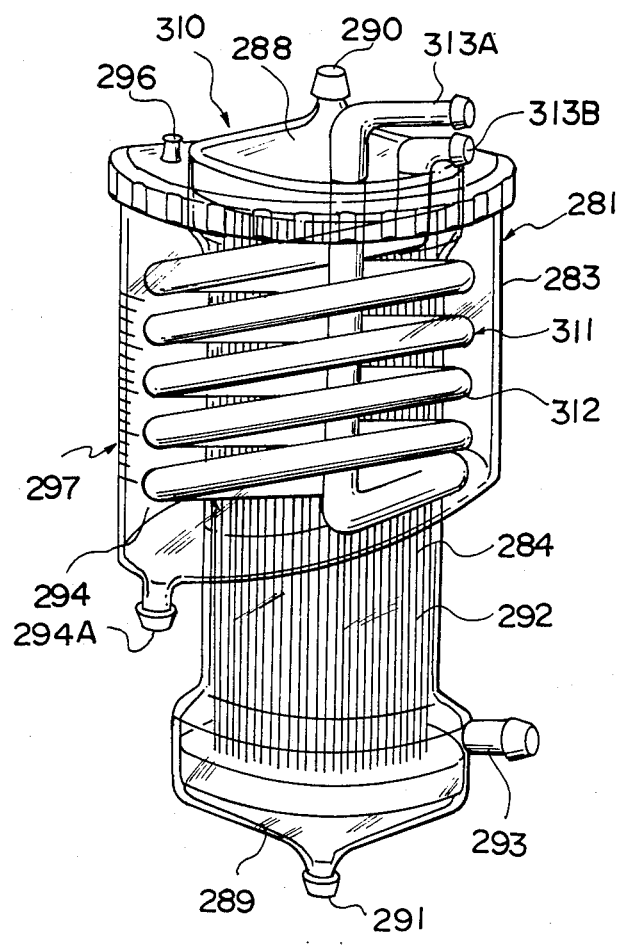
FIG. 18 is a perspective view illustrating an artificial lung according to a third embodiment.

FIG. 18 is a perspective view showing another example of the artificial lung 250.

In FIG. 18, the artificial lung, designated at 310, is substantially the same as the artificial lung 280. Portions that have the same function as those of the artificial lung 280 are designated by like reference characters and are not described again. The artificial lung 310 differs from the artificial lung 280 in that the interior of the heat exchanger tank 297 is provided with a different heat exchanger 311. In this case, the heat exchanger 311 comprises a coil-shaped tubular body 312, which is equipped with inlet and outlet ports 313A, 313B for heating and cooling water.

As with the artificial lung 250, the artificial lung 310 improves the gas exchange performance per unit membrane area of the hollow fibers 284, makes it possible to achieve perfusion of the blood by virtue of the head developed between the patient and the artificial lung 310, and reduces the quantity of blood needed to fill the blood circuit in which the artificial lung is used, thanks to the blood reservoir 294 and heat exchanger tank 297, which form part of the blood chamber 292.

FIG. 19 is a perspective view showing another example of the artificial lung 250. The artificial lung, designated at 320, has a housing 321 comprising an inner cylinder 322 and an outer cylinder 323. A bundle 325 of a multiplicity of hollow fibers 324 are accommodated within the inner cylinder 322. The ends of the hollow fibers 324 are retained liquid tightly within the inner cylinder 322 via walls 326, 327 retained in the upper and lower ends of the inner cylinder 322, respectively. A header 328 is attached to one end portion of the inner cylinder 322, and a header 329 to the other end portion thereof. The inner side of the header 328 and the wall 327 define a gas inlet chamber similar to that formed in the artificial lung 250. The inner side of the header 329 and the wall 326 define a gas outlet chamber similar to that formed in the artificial lung 250. The header 329 is formed to include a gas outlet port 331, and the header 328 is formed to include a gas inlet port 330. The inner wall of the housing 321, the outer wall of the hollow fibers 324, and the walls 326, 327 define a blood chamber 332. A blood inlet port 333 is connected to the lower end of the inner cylinder 322 through a communication portion 333A. Thus, a gas such as oxygen or air supplied from the gas inlet port 330 can be passed through the interior of the hollow fibers 324, while blood supplied from the blood inlet port 333 is passed in a turbulent state along the periphery of the hollow fibers 324 within the blood chamber 332, allowing a gas exchange to take place.

Further, in the artificial lung 320, a blood reservoir 334, which communicates with the blood chamber 332, is formed between the inner cylinder 322 and outer cylinder 323, which form the housing 321. The side wall of that portion of the inner cylinder 322 inside the outer cylinder 323 is provided with a plurality of circumferentially spaced windows or communication passages 335 for communicating the blood chamber 332 inside the inner cylinder 322 with the interior of the blood reservoir 334. The outer cylinder 323 is provided at its upper portion with a gas vent 336 communicating with the interior of the reservoir 334. The lower portion of the outer cylinder 323 is formed to include a blood outlet port 334A communicating with the reservoir 334. Thus, the blood reservoir 334 is adapted to collect blood which has undergone a gas exchange, similar to the blood reservoir 264 of the artificial lung 250.

In the housing 321, there is defined between the blood inlet port 333 and the communication passage 333A a heat exchanger tank 336 constituting part of the blood chamber 332 and accommodating a heat exchanger 335. The heat exchanger 335 is supported at both ends by a pair of walls 337, 338 located within the heat exchanger tank 336, and comprises a bundle of slender tubes 339 opening at one end into the blood inlet port 333 and at the other end into the communication passage 333A. The hollow interior of each slender tube 339 serves as a blood flow passage, while the walls 337, 338 and the outer walls of the slender tubes 339 form a flow passage for a heat transfer medium. Inlet and outlet ports 340A, 340B for cooling and heating water are connected to the flow passage for the heat transfer medium.

Thus, as with the artificial lung 250, the artificial lung 320 improves the gas exchange performance per unit membrane area of the hollow fibers 324, makes it possible to achieve perfusion of the blood by virtue of the head developed between the patient and the artificial lung 320, and reduces the quantity of blood needed to fill the blood circuit in which the artificial lung is used, thanks to the blood reservoir 324 and heat exchanger tank 336, which form part of the the blood chamber 332.

It is preferred that the heat exchanger of FIG. 19 be provided on the side of blood outflow port, as in FIG. 14, or within the blood reservoir, as in FIGS. 17 and 18. The reason is that disposing the heat exchanger at a point preceding the oxygenation apparatus will reduce the momentum of the blood provided by the head, thereby having a deleterious effect upon head-induced perfusion. However, if a hollow heat exchanger is used as shown in FIG. 19, loss of momentum is minimal and satisfactory results can be obtained. There will be little influence from external temperature and, hence, a higher heat exchange efficiency if the heat exchanger is provided within the blood reservoir or on the side of the blood outlet port.

A slender tube 342 having fins 341, as shown in FIG. 20, may be employed as the tubes forming the heat exchanger in the above embodiment.

Further, the annular blood flow passage 263A in the artificial lung 250 (FIG. 16) may be selected as the blood chamber for receiving the heat exchanger.

The actions and effects of the foregoing artificial lung will now be set forth.

As described, the hollow fiber-type artificial lung, having the heat exchanger, comprises an axially extended housing, a hollow fiber bundle having of a multiplicity of hollow fibers accommodated within and along the axial direction of the housing, the hollow fibers forming blood channels between outer wall surfaces of neighboring ones thereof, and being arranged within the housing in such a manner that neighboring blood channels are brought into substantial communication, first and second walls liquid-tightly supporting the hollow fibers at both end portions thereof within the housing, the first and second walls, the inner wall of the housing and the outer wall surfaces of the hollow fibers defining a blood chamber, a blood reservoir provided integral with the blood chamber and having its interior communicated with the blood chamber, and a heat exchanger provided integral with a blood flow passage, which is formed by the blood chamber, at least at an upstream, downstream or intermediate portion of the blood flow passage. Owing to such construction, gas exchange takes place while the blood is flowing in a turbulent state, making it possible to improve the gas exchange performance per unit membrane area. In addition, the blood flow resistance interiorly of the blood chamber is reduced to a small value, so that perfusion of the blood may be achieved owing to the head developed between the patient and the artificial lung. Furthermore, the amount of blood needed to fill the blood circuit is small owing to provision of the heat exchanger interiorly of the blood chamber.

Since the blood reservoir is provided integral with the blood chamber and communicates with the blood chamber, the blood circuit is reduced in length so that less blood is needed to fill the circuit. By placing the heat exchanger within the blood reservoir on the side of the blood outlet port, the above-described effects are enhanced and there is no loss of blood momentum provided by the head.

Further, the heat exchanger comprises a bundle of a multiplicity of slender tubes supported at both ends, which ends are open, the hollow interiors of the tubes define blood flow passages, and the heat exchanger is so adapted that a heat transfer medium may be passed along the periphery of the tubes. As a result, the blood flows through the tubes in the axial direction and meets little resistance, so there is but little loss in the blood momentum provided by the head. Operability is enhanced as well.

Since the blood reservoir has a gas vent communicating with the atmosphere, the interior of the blood reservoir is held at atmospheric pressure at all times. The outer wall of the blood reservoir consists of a rigid material, and is provided with graduations so that a change in the amount of extracorporeally circulating blood can be verified with ease.

The hollow fibers are made of microporous membrane. This diminishes membrane resistance to gas travel so that the gas exchange performance can be enhanced.

The housing comprises an inner cylinder accommodating the hollow fibers, and an outer cylinder surrounding a portion of the inner cylinder for defining the blood reservoir between itself and the inner cylinder. The first wall supporting the hollow fibers is retained in the inner cylinder, and the second wall supporting the hollow fibers is retained in the outer cylinder. This results in a comparatively simple construction. Alternatively, both the first and second walls supporting the hollow fibers may be retained in the inner cylinder to further simplify construction and facilitate manufacture.

The inner surface of the housing at a portion communicating with the blood inlet port is flared outwardly relative to the intermediate portion of the housing, thereby forming an annular blood flow passage between the outer periphery of the hollow fiber bundle and the inner surface of the housing. This makes it possible for the entrant blood to be distributed to each of the hollow fibers smoothly from the entire outer periphery of the bundle facing the blood flow passage.

The flared inner surface of the housing in the vicinity of the blood inlet port is off centered with respect to the hollow fiber bundle so as to increase the distance between the blood inlet port and the hollow fiber bundle, thereby enlarging the flow area of the blood flow passage facing the blood inlet port. As a result, the blood from the blood flow passage is distributed in a uniform amount circumferentially of the hollow fiber bundle, making it possible for the flow rate of the blood traveling axially of the housing within the blood chamber to be made uniform in relation to the circumferential direction of the hollow fiber bundle.

As many apparently widely different embodiments of the present invention can be made without departing from the spirit and scope thereof, it is to be understood that the invention is not limited to the specific embodiments thereof except as defined in the appended claims.

What is claimed is:

1. A hollow fiber-type artificial lung, comprising:
an axially extended housing;
a hollow fiber bundle including a multiplicity of hollow fibers accommodated within and along the axial direction of said housing, said hollow fibers forming blood channels between outer wall surfaces of neighboring ones of said fibers, and being arranged within said housing in such a manner that neighboring blood channels are brought into substantial communication;

first and second walls each having cylindrically concave faces for liquid-tightly supporting said hollow fibers at both end portions of said fibers within said housing;

gas inlet means provided on an outer side of at least one of said first and said second walls for communicating with the hollow interior of said hollow fibers;

the concave faces of said first and second walls, the inner wall of said housing and the outer wall surfaces of said hollow fibers defining a blood chamber, wherein the centers of the cylindrically concave faces of said first and second walls define extreme axial end locations of said blood chamber;

blood inlet and outlet means communicating with said blood chamber;

the inner surface of said housing in the vicinity of said blood inlet means being flared outwardly relative to the inner surface of the intermediate portion of the housing, for forming a first annular blood flow passage in said blood chamber at a portion adjacent to said first wall between the outer periphery of said hollow fiber bundle and the inner surface of the flared housing, wherein the flared inner surface of said housing in the vicinity of said blood inlet means is off-centered with respect to said hollow fiber hundle to increase the distance between said blood inlet means and said hollow fiber bundle and thus enlarge the flow area of said first blood flow passage facing said blood inlet means while gradually diminishing the flow area of said first blood flow passage with increasing distance from said blood inlet means, so that the amount of blood entering said first blood flow passage from said inlet means is substantially uniform circumferentially of said hollow fiber bundle and the flow rate of blood traveling axially of the housing within said blood chamber tends to be made uniform, said first blood flow passage communicates with said blood inlet means and surrounds said hollow fiber bundle circumferentially at the end portion retained by said first wall, and said housing forming a second blood flow passage at a portion adjacent to said second wall, said second flow passage communicating with said blood outlet means and surrounding said hollow fiber bundle circumferentially at the end portion retained by said second wall;

the inner surface of said housing in the vicinity of said blood outlet means being flared outwardly relative to the inner surface of the intermediate portion of said housing, for forming said second blood flow passage in an annular shape between the outer periphery of said hollow fiber bundle and the inner surface of said housing:

the flared inner surface of said housing in the vicinity of said blood outlet means is off-centered with respect to said hollow fiber bundle to increase the distance between said blood outlet means and said hollow fiber bundle and thus enlarge the flow area of said second blood flow passage facing said blood outlet means while gradually diminishing the flow area of said second blood flow passage with increasing distance from said blood outlet means so that the amount of blood entering said second blood flow passage is substantially uniform circumferentially of said hollow fiber bundle and the flow rate of blood traveling axially of said housing becomes uniform in relation to the circumferential direction of said hollow fiber bundle;

said housing having an inner diameter of minimum value at the vicinity of the central region of said housing axially thereof for constricting said hollow fiber bundle, and a gradually larger value in the direction toward the ends of the housing for varying the cross-sectional area of said blood channels formed between neighboring fibers to narrow said blood channels toward the axial center region of said hollow fiber bundle from both of its ends; and gas venting means communicating with the interior of said blood chamber in the vicinity of the center of the concave face of said second wall so that said gas venting means can be situated at substantially the highest location of said blood chamber when said housing is vertically oriented when the artificial lung is in use.

2. The artificial lung according to claim 1, wherein said gas venting means and said blood outlet means are provided at positions substantially symmetrical with respect to the axis of said housing.

3. The artificial lung according to claim 1, wherein said second wall has a concave portion on a side facing said second blood flow passage, and said gas venting means is provided in a side wall of said housing adjacent the concave portion of said second wall.

4. The artificial lung according to claim 1, wherein said hollow fibers are made of a microporous membrane.

5. The artificial lung according to claim 1, wherein said gas venting means comprising a gas venting port having a detachable filter permeable to gas and impermeable to bacteria.

6. A hollow fiber-type artificial lung, comprising:
an axially extended housing;
a hollow fiber bundle including a multiplicity of hollow fibers accommodated within and along the axial direction of said housing, said hollow fibers forming blood channels between outer wall surfaces of neighboring ones thereof, and being arranged within said housing in such a manner that neighboring blood channels are brought into substantial communication;
first and second walls liquid-tightly supporting said hollow fibers at both end portions thereof within said housing;
said first and second walls, the inner wall of said housing and the outer wall surfaces of said hollow fibers defining a blood chamber;
blood inlet means provided in a side wall of said housing in the vicinity of said first wall and communicating with said blood chamber;
the inner surface of said housing in the vicinity of said blood inlet means being flared outwardly relative to the inner surface of the intermediate portion of the housing, for forming a first annular blood flow passage in said blood chamber at a portion adjacent to said first wall between the outer periphery of said hollow fiber bundle and the inner surface of the flared housing, wherein the flared inner surface of said housing in the vicinity of said blood inlet means is off-centered with respect to said hollow fiber bundle to increase the distance between said blood inlet means and said hollow fiber bundle and thus enlarge the flow area of said first blood flow passage facing said blood inlet means while gradually diminishing the flow area of said first blood flow passage with increasing distance from said blood inlet means, so that the amount of blood entering said first blood flow passage from said inlet means is substantially uniform circumferentially of said hollow fiber bundle and the flow rate of blood traveling axially of the housing within said blood chamber tends to be made uniform;

a blood reservoir chamber provided in the vicinity of said second wall and formed integrally with said blood chamber for communicating directly with said blood chamber;

blood outlet means communicating directly with said blood reservoir chamber;

wherein said blood reservoir chamber is provided on said housing in the region of said blood outlet means and is defined in part by the outer periphery of a portion of said housing which extends along the axial direction of said blood chamber so that sufficient gas-exchange area with said blood chamber is afforded with a desired reserve volume of said blood reservoir chamber; and gas inlet means provided on an outer side of at least one of said first and second walls and communicating with the hollow interior of said hollow fibers.

7. The artificial lung according to claim 6, further comprising gas venting means communicating said blood reservoir chamber with the atmosphere.

8. The artificial lung according to claim 7, wherein said gas venting means comprises a gas venting port having a filter permeable to gas and impermeable to bacteria.

9. The artificial lung according to claim 6, wherein said blood reservoir chamber has an outer wall comprising a rigid material, a side surface of said outer wall having graduations.

10. The artifical lung according to claim 6, wherein said blood reservoir chamber is so adapted that, when blood is introduced from said blood inlet means so as to rise within said blood chamber, the blood will flow downwardly into said blood reservoir chamber from said blood chamber and will be collected within said blood reservoir chamber.

11. The artificial lung according to claim 6, wherein said housing comprises an inner cylinder defining said blood chamber, and an outer cylinder surrounding a portion of said inner cylinder for defining said blood reservoir chamber between itself and said inner cylinder, said first wall being retained in said inner cylinder, said second wall being retained in said outer cylinderr.

12. The artificial lung according to claim 6, wherein said housing comprises an inner cylinder defining said blood chamber, and an outer cylinder surrounding a portion of said inner cylinder for defining said blood reservoir chamber between itself and said inner cylinder, said first and second walls being retained in said inner cylinder.

13. The artificial lung according to claim 6, wherein said hollow fibers are made of a microporous membrane.

14. A hollow fiber-type artificial lung, comprising:
an axially extended housing;
a hollow fiber bundle including a multiplicity of hollow fibers accommodated within and along the axial direction of said housing, said hollow fibers forming blood channels between outer wall surfaces of neighboring ones thereof, and being arranged within said housing in such a manner that neighboring blood channels are brought into substantial communication;

first and second walls liquid-tightly supporting said hollow fibers at both end portions thereof within said housing;

said first and second walls, the inner wall of said housing and the outer wall surfaces of said hollow fibers defining a blood chamber;

blood inlet means provided in a side wall of said housing in the vicinity of said first wall and having an opening communicating with said blood chamber;

the inner surface of said housing in the vicinity of said blood inlet means being flared outwardly relative to the inner surface of the intermediate portion of the housing, for forming a first annular blood flow passage in said blood chamber at a portion adjacent to said first wall between the outer periphery of said hollow fiber bundle and the inner surface of the flared housing, wherein the flared inner surface of said housing in the vicinity of said blood inlet means is off-centered with respect to said hollow fiber bundle to increase the distance between said blood inlet means and said hollow fiber bundle and thus enlarge the flow area of said first blood flow passage facing said blood inlet means while gradually diminishing the flow area of said first blood flow passage with increasing distance from said blood inlet means, so that the amount of blood entering said first blood flow passage from said inlet means is substantially uniform circumferentially of said hollow fiber bundle and the flow rate of blood traveling axially of the housing within said blood chamber tends to be made uniform;

blood outlet means provided in a side wall of said housing in the vicinity of said second wall and having an opening communicating with said blood chamber;

a heat exchanger provided integral with a blood flow passage, which is formed by said blood chamber, at least at an upstream, downstream or intermediate portion of said blood flow passage;

gas inlet means provided on an outer side of at least one of said first and second walls; and a blood reservoir provided on said housing on the side of said blood outlet means and formed integrally with said blood chamber for communicating directly with said blood chamber;

wherein said blood reservoir is defined in part by the outer periphery of a portion of said housing which extends along the axial direction of said blood chamber so that sufficient gas-exchange area with said blood chamber is afforded with a desired reserve volume of said blood reservoir.

15. The artificial lung according to claim 14, wherein said heat exchanger is provided in said blood chamber on said blood outlet means.

16. The artificial lung according to claim 14, wherein said heat exchanger is provided within said blood reservoir.

17. The artificial lung according to claim 14, wherein said housing has a blood inlet port, said heat exchanger being provided on the side of said blood inlet port.

18. The artificial lung according to claim 14, wherein said heat exchanger comprises a bundle of a multiplicity of slender tubes supported at both ends, which ends are open, the hollow interiors of said tubes defining blood flow passages, said heat exchanger being so adapted that a heat transfer medium may be passed along the periphery of said tubes.

19. The artificial lung according to claim 14, wherein said heat exchanger comprises a tubular body through the hollow interior of which a heat transfer medium may be passed.

20. The artificial lung according to claim 14, wherein said blood reservoir has a gas vent communicating with the atmosphere.

21. The artificial lung according to claim 14, wherein said blood reservoir has an outer wall comprising a rigid material, said outer wall having graduations.

22. The artificial lung according to claim 14, wherein said hollow fibers are made of microporous membrane.

23. The artificial lung according to claim 14, wherein said housing comprises an inner cylinder accommodating said hollow fibers, and an outer cylinder surrounding a portion of said inner cylinder for defining said blood reservoir between said outer cylinder and said inner cylinder, said first wall supporting said hollow fibers being retained in said inner cylinder, said second wall supporting said hollow fibers being retained in said outer cylinder.

24. The artificial lung according to claim 14, wherein said housing comprises an inner cylinder accommodating said hollow fibers, and an outer cylinder surrounding a portion of said inner cylinder for defining said blood reservoir between itself and said inner cylinder, said first and second walls supporting said hollow fibers being retained in said inner cylinder.

* * * * *

UNITED STATES PATENT AND TRADEMARK OFFICE
CERTIFICATE OF CORRECTION

PATENT NO. : 4,620,965
DATED : November 4, 1986
INVENTOR(S) : H. Fukusawa et al.

It is certified that error appears in the above-identified patent and that said Letters Patent is hereby corrected as shown below:

Column 5, line 6, change "housing 5" to -- housing 15 --.

Column 26, line 51 (claim 11), change "cylinderr" to

-- cylinder --.

Signed and Sealed this

Seventeenth Day of March, 1987

Attest:

DONALD J. QUIGG

*Attesting Officer*   *Commissioner of Patents and Trademarks*